(12) United States Patent
Whittaker et al.

(10) Patent No.: US 7,655,011 B2
(45) Date of Patent: *__Feb. 2, 2010__

(54) METHOD AND APPARATUS FOR FIXING A GRAFT IN A BONE TUNNEL

(75) Inventors: Gregory R. Whittaker, Stoneham, MA (US); Ronald L. Taylor, Jr., Everett, MA (US)

(73) Assignee: Ethicon, Inc., Somerville, NJ (US)

( * ) Notice: Subject to any disclaimer, the term of this patent is extended or adjusted under 35 U.S.C. 154(b) by 372 days.

This patent is subject to a terminal disclaimer.

(21) Appl. No.: 11/088,250

(22) Filed: Mar. 23, 2005

(65) Prior Publication Data

US 2005/0234469 A1    Oct. 20, 2005

Related U.S. Application Data

(63) Continuation of application No. 10/364,786, filed on Feb. 11, 2003, now Pat. No. 6,958,067, which is a continuation of application No. 09/865,274, filed on May 25, 2001, now Pat. No. 6,517,546.

(60) Provisional application No. 60/275,431, filed on Mar. 13, 2001.

(51) Int. Cl.
*A61B 17/58* (2006.01)
*A61B 17/60* (2006.01)

(52) U.S. Cl. .............. 606/98; 606/96; 606/80

(58) Field of Classification Search ............ 606/96, 606/80, 98, 86, 87, 102, 104, 64, 65, 66, 606/67, 68

See application file for complete search history.

(56) References Cited

U.S. PATENT DOCUMENTS

| | | | |
|---|---|---|---|
| 2,112,337 A * | 3/1938 | Gillespie | ............ 19/122 |
| 3,973,277 A | 8/1976 | Semple et al. | |
| 4,022,191 A | 5/1977 | Jamshidi | |
| 4,257,411 A | 3/1981 | Cho | |
| 4,431,200 A | 2/1984 | Sugimura | |
| 4,541,424 A * | 9/1985 | Grosse et al. | ............ 606/98 |
| 4,792,336 A | 12/1988 | Hlavacek et al. | |
| 4,809,694 A | 3/1989 | Ferrara | |
| 4,898,156 A | 2/1990 | Gatturna et al. | |
| 4,899,743 A | 2/1990 | Nicholson et al. | |
| 4,901,711 A | 2/1990 | Goble et al. | |
| 4,950,270 A | 8/1990 | Bowman et al. | |
| 4,968,315 A | 11/1990 | Gatturna | |
| 4,985,032 A | 1/1991 | Goble | |
| 4,986,833 A | 1/1991 | Worland | |
| 5,004,474 A | 4/1991 | Fronk et al. | |
| 5,013,318 A * | 5/1991 | Spranza, III | ............ 606/102 |
| 5,031,634 A | 7/1991 | Simon | |
| 5,053,042 A | 10/1991 | Bidwell | |
| 5,067,962 A | 11/1991 | Campbell et al. | |
| 5,080,673 A | 1/1992 | Burkhead et al. | |
| 5,100,387 A | 3/1992 | Ng | |
| 5,108,446 A | 4/1992 | Wagner et al. | |

(Continued)

FOREIGN PATENT DOCUMENTS

DE    19510372    7/1996

(Continued)

*Primary Examiner*—Pedro Philogene

(57) ABSTRACT

A method and apparatus for fixing a ligament in a bone tunnel by cross-pinning the ligament in the bone tunnel.

24 Claims, 36 Drawing Sheets

U.S. PATENT DOCUMENTS

| | | | |
|---|---|---|---|
| 5,147,362 A | 9/1992 | Goble | |
| 5,152,764 A | 10/1992 | Goble | |
| 5,154,720 A | 10/1992 | Trott et al. | |
| 5,192,322 A | 3/1993 | Koch et al. | |
| 5,201,742 A | 4/1993 | Hasson | |
| 5,235,987 A | 8/1993 | Wolfe | |
| 5,266,075 A | 11/1993 | Clark et al. | |
| 5,298,012 A | 3/1994 | Handlos | |
| 5,312,409 A | 5/1994 | McLaughlin et al. | |
| 5,314,429 A * | 5/1994 | Goble | 606/96 |
| 5,314,487 A | 5/1994 | Schryver et al. | |
| 5,316,014 A | 5/1994 | Livingston | |
| 5,320,111 A | 6/1994 | Livingston | |
| 5,350,380 A * | 9/1994 | Goble et al. | 606/80 |
| 5,354,300 A | 10/1994 | Goble et al. | |
| 5,356,413 A | 10/1994 | Martins et al. | |
| 5,356,435 A | 10/1994 | Thein et al. | |
| 5,372,599 A | 12/1994 | Martins | |
| 5,376,119 A | 12/1994 | Zimmermann et al. | |
| 5,393,302 A | 2/1995 | Clark et al. | |
| 5,397,356 A | 3/1995 | Goble et al. | |
| 5,431,651 A | 7/1995 | Goble | |
| 5,494,039 A | 2/1996 | Onik et al. | |
| 5,530,380 A * | 6/1996 | Kondoh | 326/98 |
| 5,562,671 A | 10/1996 | Goble et al. | |
| 5,601,562 A | 2/1997 | Wolf et al. | |
| 5,647,373 A | 7/1997 | Paltieli et al. | |
| 5,674,224 A | 10/1997 | Howell et al. | |
| 5,681,320 A * | 10/1997 | McGuire | 606/104 |
| 5,688,284 A | 11/1997 | Chervitz et al. | |
| 5,702,447 A | 12/1997 | Walch et al. | |
| 5,868,673 A | 2/1999 | Vesely | |
| 5,891,150 A * | 4/1999 | Chan | 606/96 |
| 5,911,707 A | 6/1999 | Wolvek et al. | |
| 5,916,175 A | 6/1999 | Bauer et al. | |
| 5,918,604 A * | 7/1999 | Whelan | 128/898 |
| 5,931,840 A | 8/1999 | Goble et al. | |
| 5,941,889 A | 8/1999 | Cermak | |
| 5,954,670 A | 9/1999 | Baker | |
| 5,984,930 A | 11/1999 | Maciunas et al. | |
| 6,027,506 A | 2/2000 | Faccioli et al. | |
| D422,706 S | 4/2000 | Bucholz et al. | |
| 6,048,321 A | 4/2000 | McPherson et al. | |
| 6,132,433 A | 10/2000 | Whelan | |
| 6,187,011 B1 * | 2/2001 | Torrie | 606/96 |
| 6,195,577 B1 | 2/2001 | Truwit et al. | |
| 6,203,499 B1 | 3/2001 | Imling | |
| 6,216,029 B1 | 4/2001 | Paltieli | |
| 6,231,565 B1 | 5/2001 | Tovey et al. | |
| 6,231,585 B1 | 5/2001 | Takahashi et al. | |
| 6,236,875 B1 | 5/2001 | Bucholz et al. | |
| 6,245,028 B1 | 6/2001 | Furst et al. | |
| 6,254,606 B1 * | 7/2001 | Carney et al. | 606/102 |
| 6,280,472 B1 | 8/2001 | Boucher et al. | |
| 6,283,942 B1 | 9/2001 | Staehlin et al. | |
| 6,306,138 B1 | 10/2001 | Clark et al. | |
| 6,342,056 B1 | 1/2002 | Mac-Thiong et al. | |
| 6,361,499 B1 | 3/2002 | Bates et al. | |
| 6,379,307 B1 | 4/2002 | Filly et al. | |
| 6,400,979 B1 | 6/2002 | Stoianovici et al. | |
| 6,443,960 B1 | 9/2002 | Brabrand et al. | |
| 6,445,943 B1 | 9/2002 | Ferre et al. | |
| 6,468,226 B1 | 10/2002 | McIntyre, IV | |
| 6,475,152 B1 | 11/2002 | Kelly, Jr. et al. | |
| 6,490,467 B1 | 12/2002 | Bucholz et al. | |
| 6,501,981 B1 | 12/2002 | Schweikard et al. | |
| 6,517,546 B2 | 2/2003 | Whittaker et al. | |
| 6,529,765 B1 | 3/2003 | Franck et al. | |
| 6,535,756 B1 | 3/2003 | Ruch et al. | |
| 6,539,121 B1 | 3/2003 | Haskell et al. | |
| 6,546,279 B1 | 4/2003 | Bova et al. | |
| 6,547,782 B1 | 4/2003 | Taylor | |
| 6,632,245 B2 | 10/2003 | Kim | |
| 6,665,554 B1 | 12/2003 | Charles et al. | |
| 6,687,531 B1 | 2/2004 | Ferre et al. | |
| 6,723,106 B1 | 4/2004 | Charles et al. | |
| 6,723,125 B2 | 4/2004 | Heckele et al. | |
| 6,731,966 B1 | 5/2004 | Spigelman et al. | |
| 6,770,027 B2 | 8/2004 | Banik et al. | |
| 6,770,076 B2 | 8/2004 | Foerster | |
| 6,782,288 B2 | 8/2004 | Truwit et al. | |
| 6,783,524 B2 | 8/2004 | Anderson et al. | |
| 6,785,572 B2 | 8/2004 | Yanof et al. | |
| 6,958,067 B2 | 10/2005 | Whittaker et al. | |
| 7,021,173 B2 | 4/2006 | Stoianovici et al. | |
| 7,076,106 B2 | 7/2006 | Haskell et al. | |
| 7,195,642 B2 | 3/2007 | McKernan et al. | |
| 2001/0018619 A1 | 8/2001 | Enzerink et al. | |
| 2001/0044659 A1 | 11/2001 | Laboureau et al. | |
| 2002/0165611 A1 | 11/2002 | Enzerink et al. | |
| 2003/0100814 A1 | 5/2003 | Kindlein | |

FOREIGN PATENT DOCUMENTS

| | | |
|---|---|---|
| FR | 2716364 | 8/1995 |
| JP | 2000210311 | 8/2000 |
| WO | 98/35621 | 8/1998 |
| WO | 99/52453 | 10/1999 |
| WO | 02/071958 | 9/2002 |
| WO | 03/037163 | 5/2003 |

* cited by examiner

METHOD AND APPARATUS FOR FIXING A GRAFT IN A BONE TUNNEL

REFERENCE TO PENDING PRIOR PATENT APPLICATIONS

This is a continuation of prior U.S. patent application Ser. No. 10/364,786, filed Feb. 11, 2003 now U.S. Pat. No. 6,958,067 by Gregory R. Whittaker et al. for METHOD AND APPARATUS FOR FIXING A GRAFT IN A BONE TUNNEL, which in turn is a continuation of prior U.S. patent application Ser. No. 09/865,274, filed May 25, 2001 now U.S. Pat. No. 6,517,546 by Gregory R. Whittaker et al. for METHOD AND APPARATUS FOR FIXING A GRAFT IN A BONE TUNNEL, which in turn claims benefit of prior U.S. Provisional Patent Application Ser. No. 60/275,431, filed Mar. 13, 2001 by Gregory Whittaker for METHOD AND APPARATUS FOR FIXING A GRAFT IN A TIBIAL TUNNEL. The above-identified patent applications are hereby incorporated herein by reference.

FIELD OF THE INVENTION

This invention relates to surgical methods and apparatus in general, and more particularly to methods and apparatus for fixing a graft in a bone tunnel.

BACKGROUND OF THE INVENTION

The complete or partial detachment of ligaments, tendons and/or other soft tissues from their associated bones within the body are relatively commonplace injuries. Tissue detachment may occur as the result of an accident such as a fall, overexertion during a work-related activity, during the course of an athletic event, or in any one of many other situations and/or activities. Such injuries are generally the result of excess stress being placed on the tissues.

In the case of a partial detachment, commonly referred to under the general term "sprain", the injury frequently heals itself, if given sufficient time and if care is taken not to expose the injury to undue stress during the healing process. If, however, the ligament or tendon is completely detached from its associated bone or bones, or if it is severed as the result of a traumatic injury, partial or permanent disability may result. Fortunately, a number of surgical procedures exist for re-attaching such detached tissues and/or completely replacing severely damaged tissues.

One such procedure involves the re-attachment of the detached tissue using "traditional" attachment devices such as staples, sutures and/or cancellous bone screws. Such traditional attachment devices have also been used to attach tendon or ligament grafts (often formed from autogenous tissue harvested from elsewhere in the body) to the desired bone or bones.

Another procedure is described in U.S. Pat. No. 4,950,270, issued Aug. 21, 1990 to Jerald A. Bowman et al. In this procedure, a damaged anterior cruciate ligament ("ACL") in a human knee is replaced by first forming bone tunnels through the tibia and femur at the points of normal attachment of the anterior cruciate ligament. Next, a graft ligament, with a bone block on one of its ends, is sized so as to fit within the bone tunnels. Suture is then attached to the bone block, and the suture is thereafter passed through the tibial tunnel and then the femoral tunnel. The bone block is then drawn up through the tibial tunnel and up into the femoral tunnel using the suture. As this is done, the graft ligament extends back out the femoral tunnel, across the interior of the knee joint, and then out through the tibial tunnel. The free end of the graft ligament resides outside the tibia, at the anterior side of the tibia. Next, a bone screw is inserted between the bone block and the wall of femoral bone tunnel so as to securely lock the bone block in position by a tight interference fit. Finally, the free end of the graft ligament is securely attached to the tibia.

In U.S. Pat. No. 5,147,362, issued Sep. 15, 1992 to E. Marlowe Goble, there is disclosed a procedure wherein aligned femoral and tibial tunnels are formed in a human knee. A bone block, with a graft ligament attached thereto, is passed through the tibial and femoral tunnels to a blind end of the femoral tunnel, where the block is fixed in place by an anchor. The graft ligament extends out the tibial tunnel, and the proximal end thereof is attached to the tibial cortex by staples or the like. Alternatively, the proximal end of the ligament may be fixed in the tibial tunnel by an anchor or by an interference screw.

Various types of ligament and/or suture anchors, and anchors for attaching other objects to bone, are also well known in the art. A number of these devices are described in detail in U.S. Pat. Nos. 4,898,156; 4,899,743; 4,968,315; 5,356,413; and 5,372,599.

One known method for anchoring bone blocks in bone tunnels is through "cross-pinning", in which a pin, screw or rod is driven into the bone, transversely to the bone tunnel, so as to intersect the bone block and thereby "cross-pin" the bone block in the bone tunnel.

In this respect it should be appreciated that the cross-pin (i.e., the aforementioned pin, screw or rod) is generally placed in a pre-drilled transverse passageway. In order to provide for proper cross-pinning of the bone block in the bone tunnel, a drill guide is generally used. The drill guide serves to ensure that the transverse passageway is positioned in the bone so that the transverse passageway intersects the appropriate tunnel section and hence the bone block. Drill guides for use in effecting such transverse drilling are shown in U.S. Pat. Nos. 4,901,711; 4,985,032; 5,152,764; 5,350,380; and 5,431,651.

Other patents in which cross-pinning is discussed include U.S. Pat. Nos. 3,973,277; 5,004,474; 5,067,962; 5,266,075; 5,356,435; 5,376,119; 5,393,302; and 5,397,356.

Cross-pinning methods and apparatus currently exist for fixing a graft ligament in a femoral bone tunnel. However, the femoral cross-pinning methods and apparatus that are presently known in the art do not address the use of a cross-pin in a tibial bone tunnel, which involves a different set of considerations. Among these considerations are anatomical geometries, bone configurations, bone quality, etc.

Accordingly, there exists a need for a method and apparatus for positioning at least one cross-pin so as to fix a graft in a tibial bone tunnel.

There also exists a need for a method and apparatus for positioning at least one cross-pin across a tibial tunnel such that, upon completion of the procedure, the cross-pin is located in the cortical portion of the tibia, adjacent to the tibial plateau.

SUMMARY OF THE INVENTION

One object of the present invention is, therefore, to provide a novel method and apparatus for positioning at least one cross-pin so as to fix a graft in a tibial bone tunnel.

Another object of the present invention is to provide a novel method and apparatus for positioning at least one cross-pin across a tibial tunnel such that, upon completion of the procedure, the cross-pin is located in the tibia and, more preferably, in the cortical portion of the tibia, adjacent to the tibial plateau.

These and other objects of the present invention are addressed by the provision and use of a novel method and apparatus for fixing a graft in a bone tunnel.

In accordance with a feature of the present invention, there is provided apparatus for positioning at least one cross-pin in a bone through a bone tunnel, the apparatus comprising: a bone tunnel guide rod having a proximal end and a distal end; a movable element slidably positioned about the bone tunnel guide rod, wherein said movable element is lockable into a position to selectively adjust the length of said guide rod between said distal end and said movable element; a frame member having a base portion and an arm portion, the base portion attachable to the proximal end of the bone tunnel guide rod; a drill guide member attachable to the arm portion of the frame member; and drilling means for drilling at least one cross-pin hole in the bone and across the bone tunnel, with the drilling means being supported in position by the drill guide member, the drill guide member being in attachment with the frame member, the frame member being in attachment with the bone tunnel guide rod, and the bone tunnel guide rod being inserted into the bone tunnel, and the apparatus being held against the bone, with the movable element limiting further insertion into the bone tunnel.

In accordance with a further feature of the present invention, there is provided a method for fixing a ligament in a bone tunnel, the method comprising the steps of: forming a bone tunnel in a bone, the bone tunnel comprising a first open end and a second open end, with a portion between the first open end and the second open end having a diameter sized to receive the ligament; inserting a guide rod into the bone tunnel, the guide rod having a proximal end and a distal end; positioning the distal end of the guide rod adjacent to the second open end of the bone tunnel; positioning a movable element on the guide rod against the bone at the first open end of the bone tunnel; drilling at least one cross-pin hole transversely through the bone and across the bone tunnel, using drilling means for drilling the cross-pin hole, the drilling means being supported in position by a drill guide member, with that drill guide member being in attachment with a frame member, the frame member being In attachment with the bone tunnel guide rod, the bone tunnel guide rod being inserted into the bone tunnel, and with the movable element limiting further insertion of the bone tunnel guide rod into the bone tunnel; and inserting at least one cross-pin through at least one cross-pin hole.

In accordance with a further feature of the present invention, there is provided an apparatus for positioning at least one cross-pin in a bone through a bone tunnel, the apparatus comprising: a bone tunnel guide rod having a proximal end and a distal end, with the bone tunnel guide rod having a gradiated index between the proximal end and the distal end, wherein the gradiated index is read at a given position in the bone tunnel in relation to an intended position of at least one cross-pin hole; a frame member having a base portion and an arm portion, the base portion attachable adjacent to the proximal end of the bone tunnel guide rod, and the arm portion of the frame member having a scale corresponding with the gradiated index of the bone tunnel guide rod; a drill guide member attachable to the arm portion of the frame member, the drill guide member being selectively adjustable relative to the scale of the frame member; and drilling means for drilling the at least one cross-pin hole in the bone through the bone tunnel, the drilling means being supported in position by the drill guide member, the drill guide member being in attachment with the frame member, and the frame member being in attachment with the bone tunnel guide rod, with the bone tunnel guide rod being inserted into the bone tunnel, with the distal end of apparatus being held against a terminal end of the bone tunnel, limiting further insertion into the bone tunnel.

In accordance with a further feature of the present invention, there is provided a method for fixing a ligament in a bone tunnel, the method comprising the steps of: forming a bone tunnel in a bone, the bone tunnel comprising a first portion and a second portion, the first portion having a first open end and a second open end, and the second portion having a third open end and a fourth terminal end, and a portion between the first open end and the fourth terminal end having a diameter sized to receive the ligament; inserting a bone tunnel guide rod into the bone tunnel, the bone tunnel guide rod having a proximal end and a distal end, and the bone tunnel guide rod having a gradiated index between the proximal end and the distal end; positioning the distal end of the guide rod against the fourth terminal end of the bone tunnel; determining the position of the gradiated index relative to the second open end of the bone tunnel; positioning a drill guide attached to a frame member, the frame member including a scale corresponding with the gradiated index of the bone tunnel guide rod, the drill guide being positioned relative to the scale in accordance with the gradiated index relative to the second open end of the bone tunnel; drilling at least one cross-pin hole transversely through the bone into the bone tunnel using drilling means for drilling the cross-pin hole, the drilling means supported in position by the drill guide member, the drill guide member being in attachment with the frame member, the frame member being in attachment with the bone tunnel guide rod, the bone tunnel guide rod being inserted into the bone tunnel, and the fourth terminal end of the bone tunnel limiting further insertion into the bone tunnel; and inserting at least one cross-pin through the cross-pin hole.

In accordance with a further feature of the present invention, there is provided an apparatus for positioning at least one cross-pin in a bone through a bone tunnel, the apparatus comprising: a kit of bone tunnel guide rods, each of the bone tunnel guide rods including a proximal end and a distal end, and each of the bone tunnel guide rods including insertion limiting means for limiting insertion into the bone tunnel, the insertion limiting means of each of the bone tunnel guide rods being located a given distance from its distal end, the kit including at least two bone tunnel guide rods, with the given distance of each of the bone tunnel guide rods being different from one another, and wherein selection from the kit is made by inserting at least one of the bone tunnel guide rods into the bone tunnel and selecting a bone tunnel guide rod that has its distal end aligned with a bone surface when said insertion limiting means is in engagement with another bone surface; a frame member having a base portion and an arm portion, the base portion attachable adjacent to the proximal end of the selected bone tunnel guide rod; a drill guide member attached to the arm portion of the frame member; drilling means for drilling the at least one cross-pin hole in the bone through the bone tunnel, the drilling means being supported in position by the drill guide member, the drill guide member being in attachment with the frame member, and the frame member being in attachment with the selected bone tunnel guide rod, with the selected bone tunnel guide rod being inserted into the bone tunnel, and with the insertion limiting means preventing further insertion into the bone tunnel.

In accordance with a further feature of the present invention, there is provided a method for fixing a ligament in a bone tunnel, the method comprising the steps of: forming a bone tunnel in a bone, the bone tunnel comprising a first open end and a second open end, with a portion between the first open end and the second open end having a diameter sized to receive the ligament; inserting at least one guide rod from a kit of bone tunnel guide rods into the bone tunnel, each of the bone tunnel guide rods including a proximal end and a distal end, and each of the bone tunnel guide rods including insertion limiting means for limiting insertion into the bone tunnel, the insertion limiting means of each of the bone tunnel guide rods being located a given distance from its distal end, the kit including at least two bone tunnel guide rods, with the given distance of each of the bone tunnel guide rods being different from one another; inserting at least one of the bone tunnel guide rods into the bone tunnel and selecting a bone tunnel guide rod that has its distal end aligned with the second end of the bone tunnel when the insertion limiting means is in engagement with the bone adjacent the first end of the bone tunnel; drilling at least one cross-pin hole transversely through the bone and across the bone tunnel, using drilling means for drilling the cross-pin hole, the drilling means being supported in position by a drill guide member, with the drill guide member being in attachment with a frame member, the frame member being in attachment with the selected bone tunnel guide rod, the selected bone tunnel guide rod being inserted into the bone tunnel, and with the insertion limiting means limiting further insertion of the bone tunnel guide rod into the bone tunnel; and inserting at least one cross-pin through said at least one cross-pin hole.

BRIEF DESCRIPTION OF THE DRAWINGS

The above and other objects and features of the present invention will be more fully discussed in, or rendered obvious by, the following detailed description of the preferred embodiments of the invention, which is to be considered together with the accompanying drawings wherein like numbers refer to like parts, and further wherein.

DETAILED DESCRIPTION OF THE PREFERRED EMBODIMENTS

Figure 1:
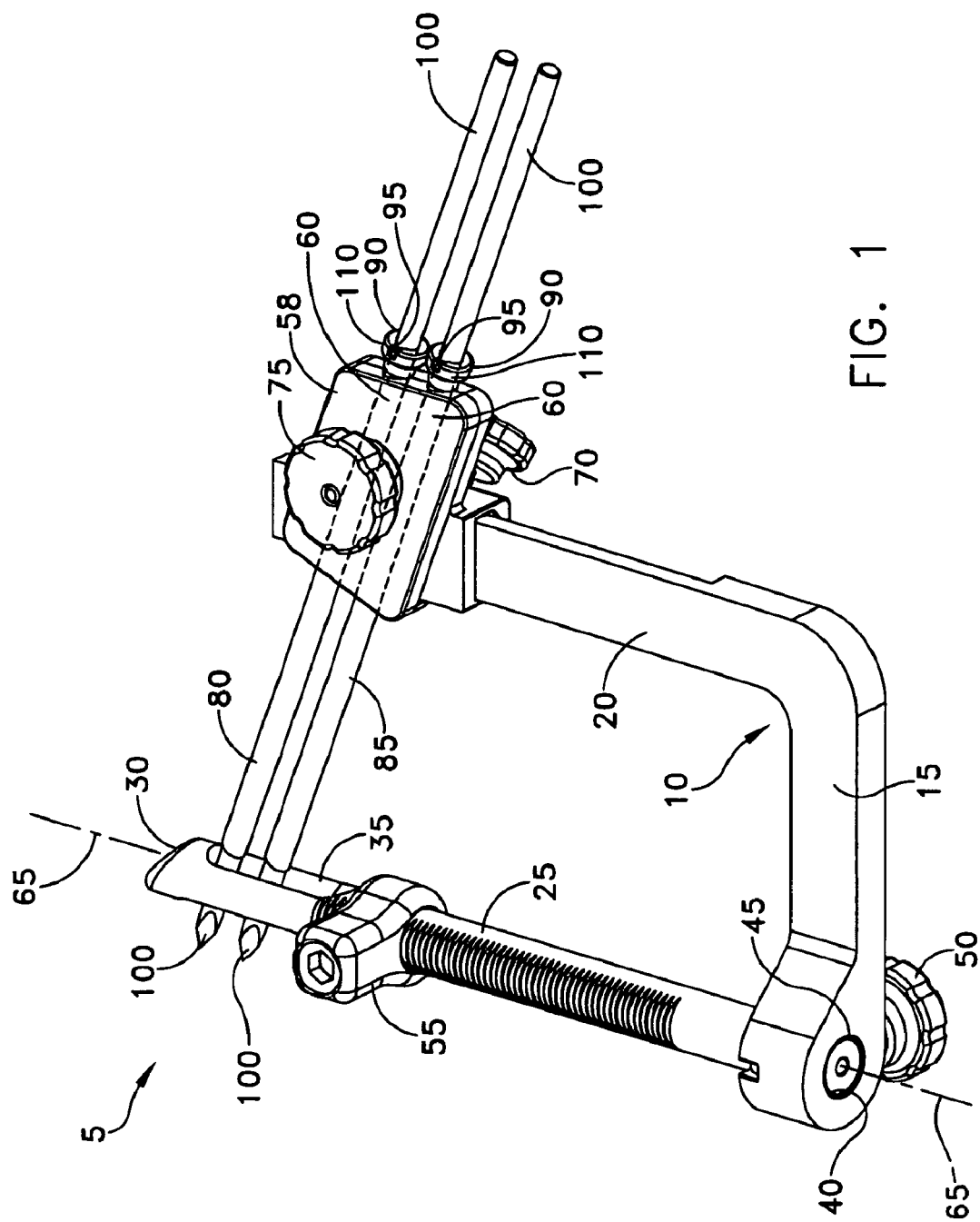
FIG. 1-13 are various views of one form of a cross-pin guide assembly for use in cross-pinning a graft in a tibial tunnel, illustrative of one preferred embodiment of the present invention.
Figure 2:
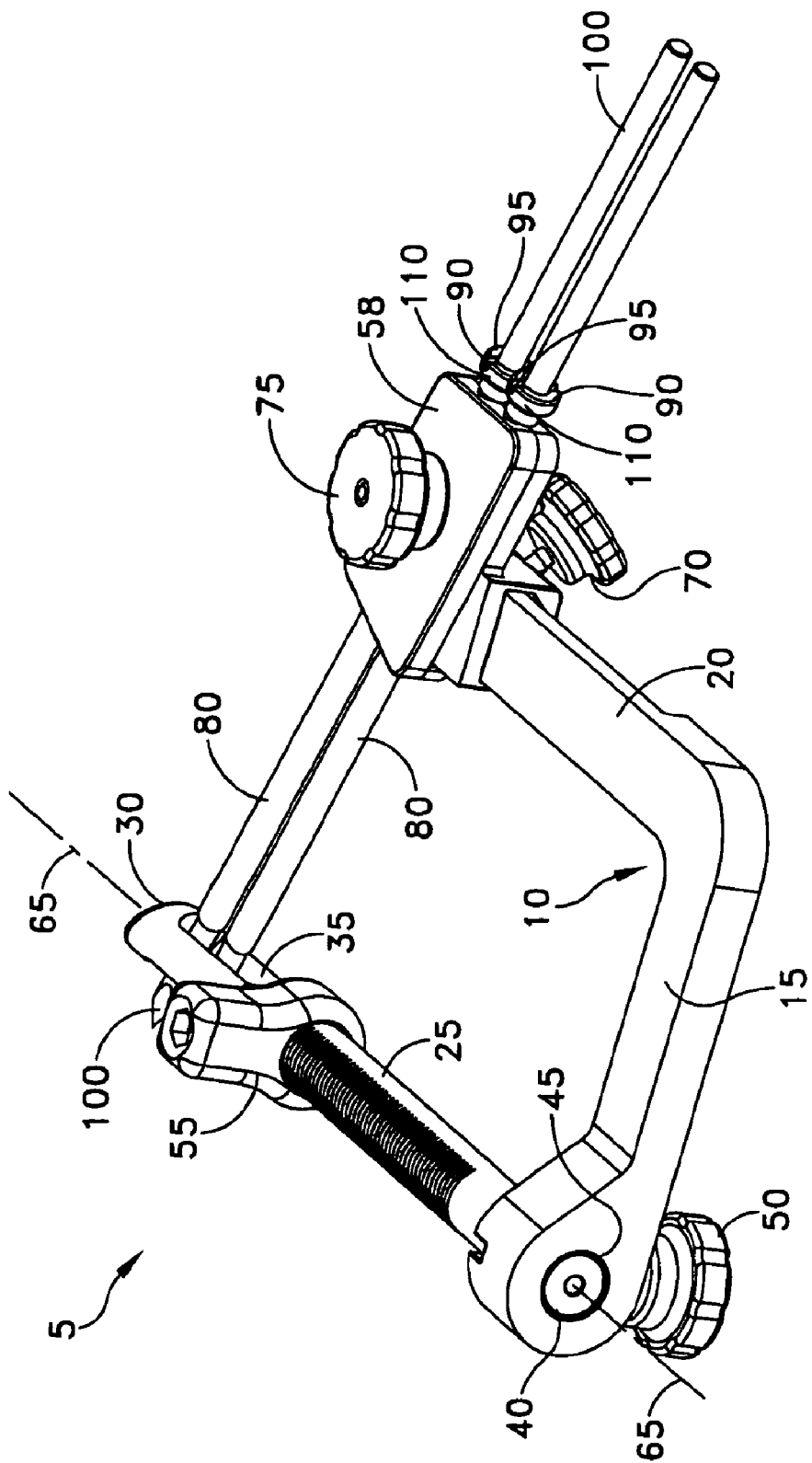
Figure 3:
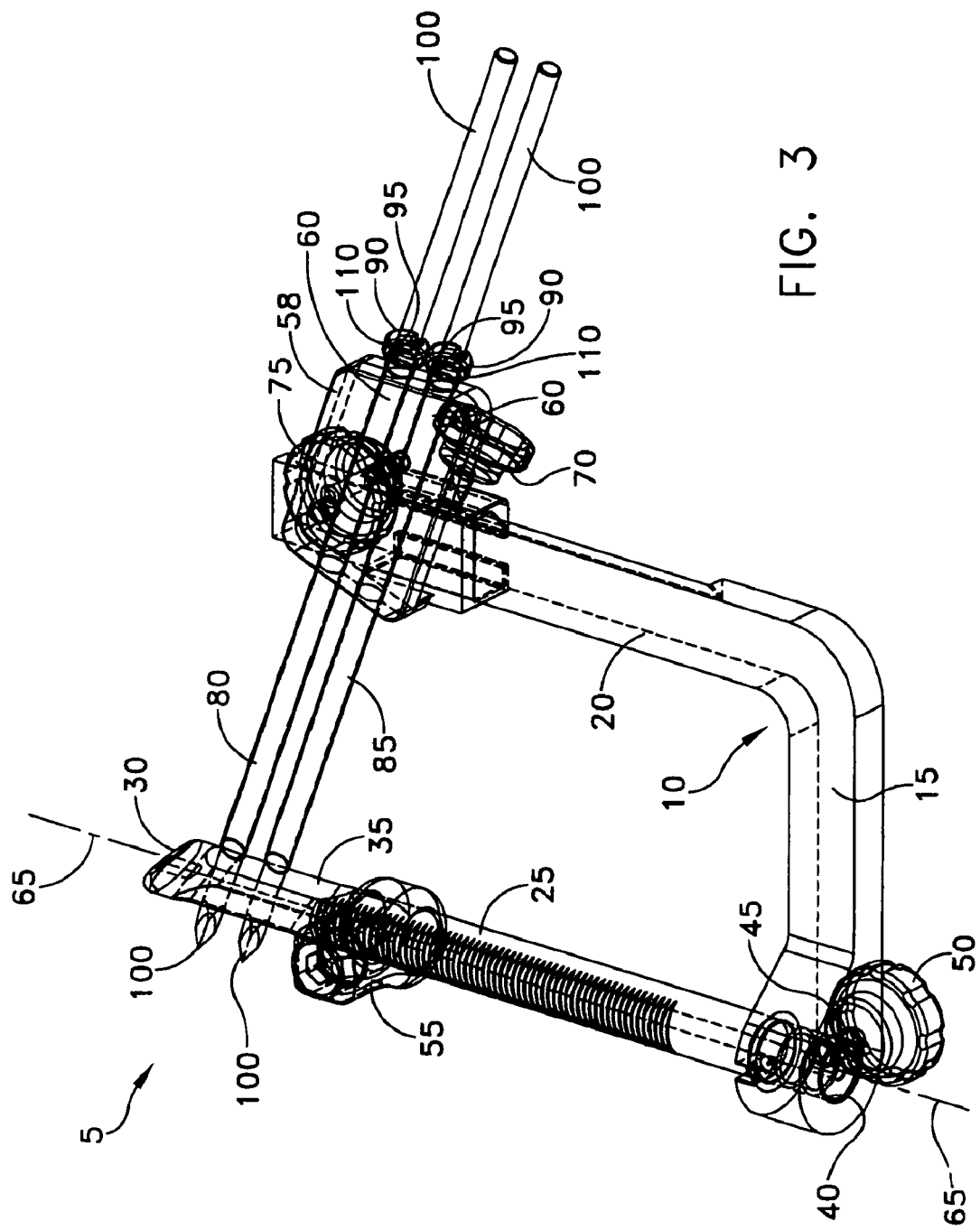
Figure 4:
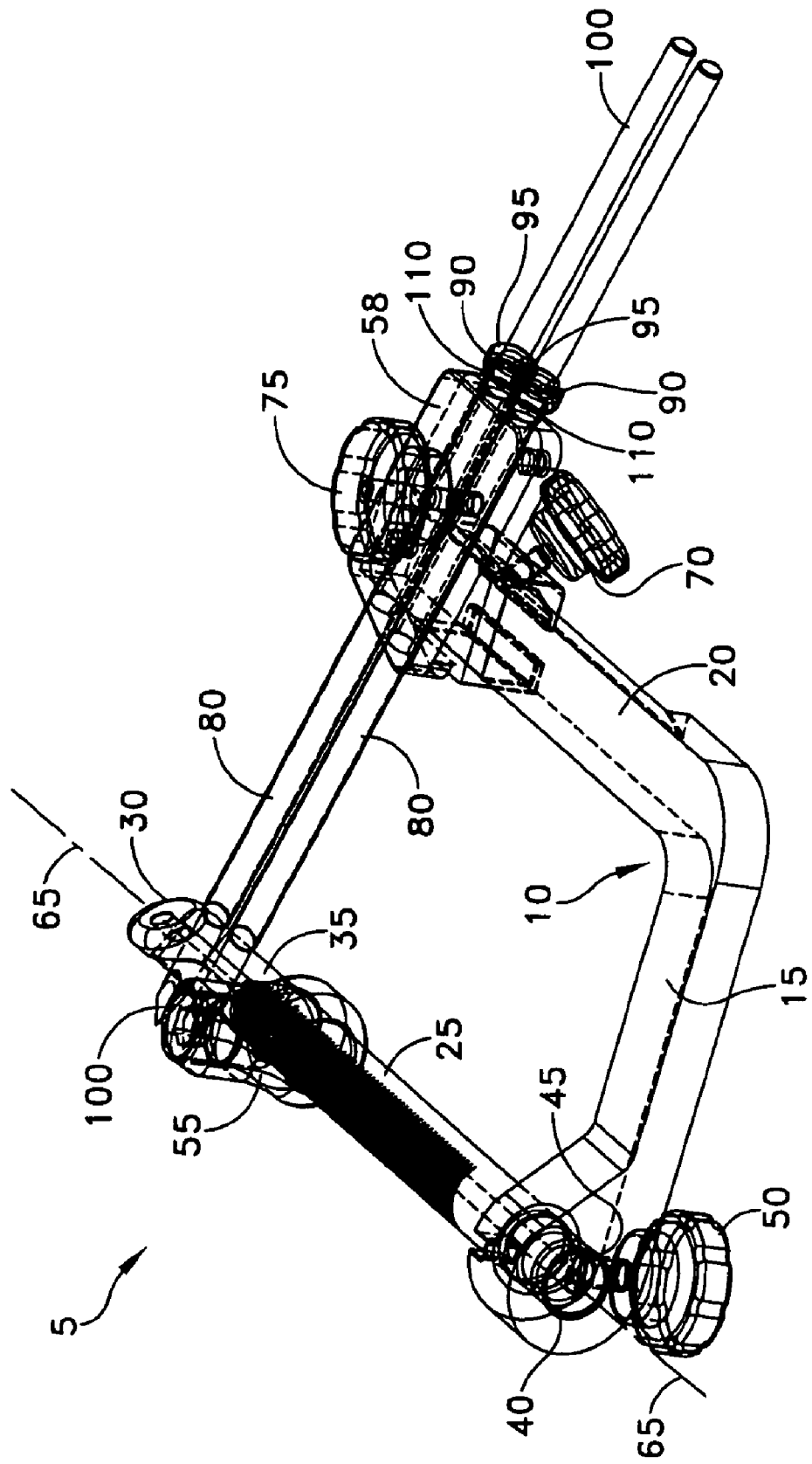
Figure 5:
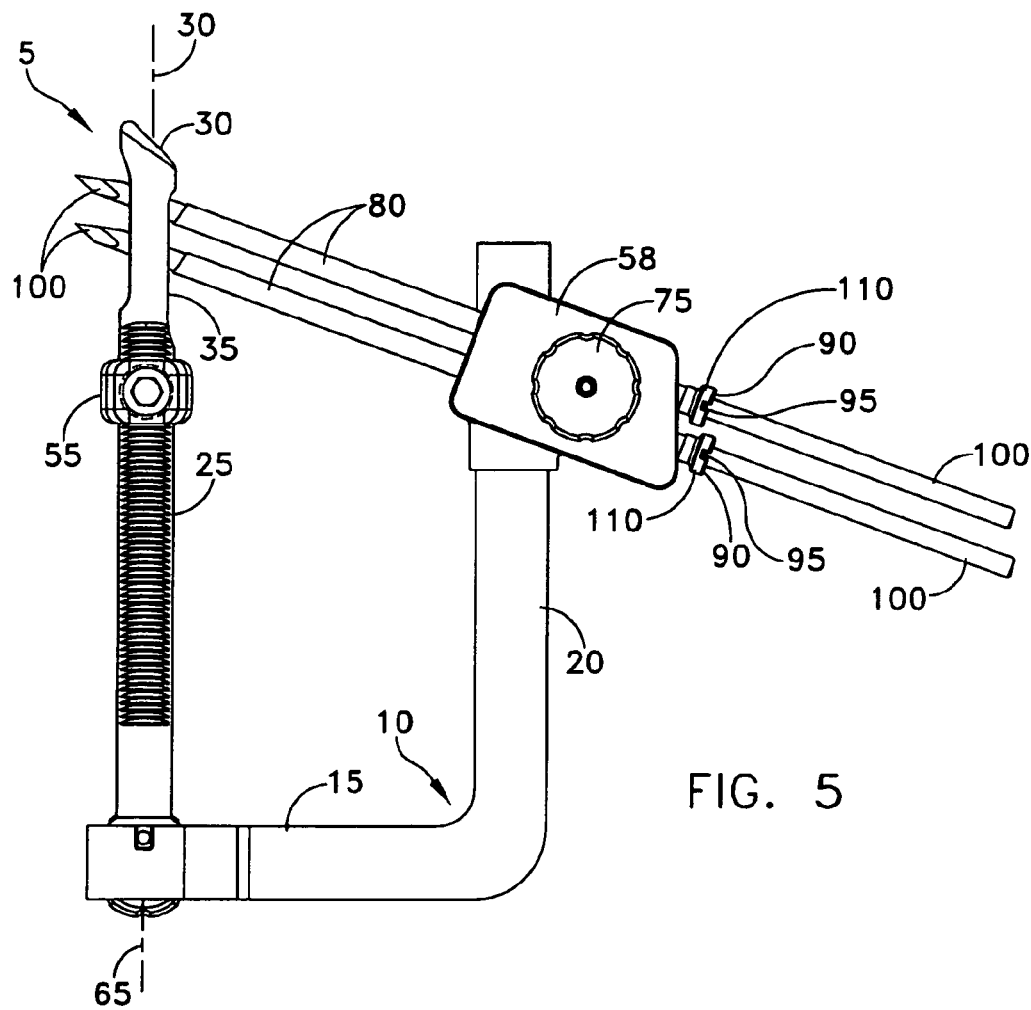
Figure 7:
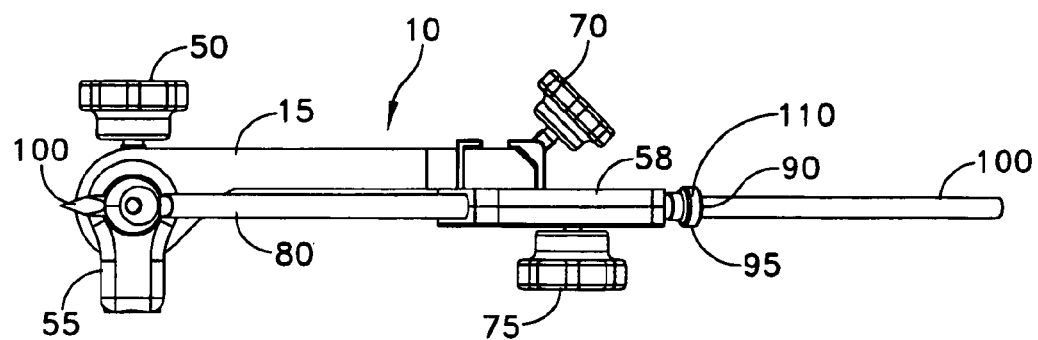
Figure 6:
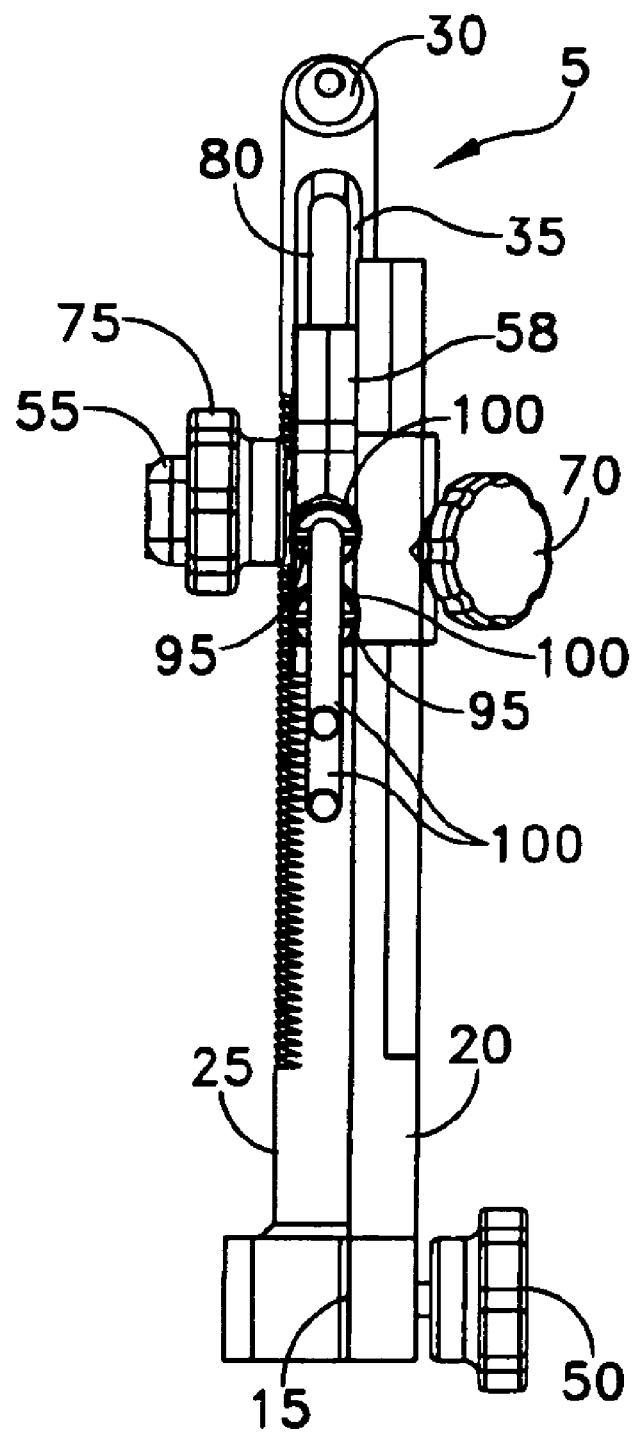
Figure 8:
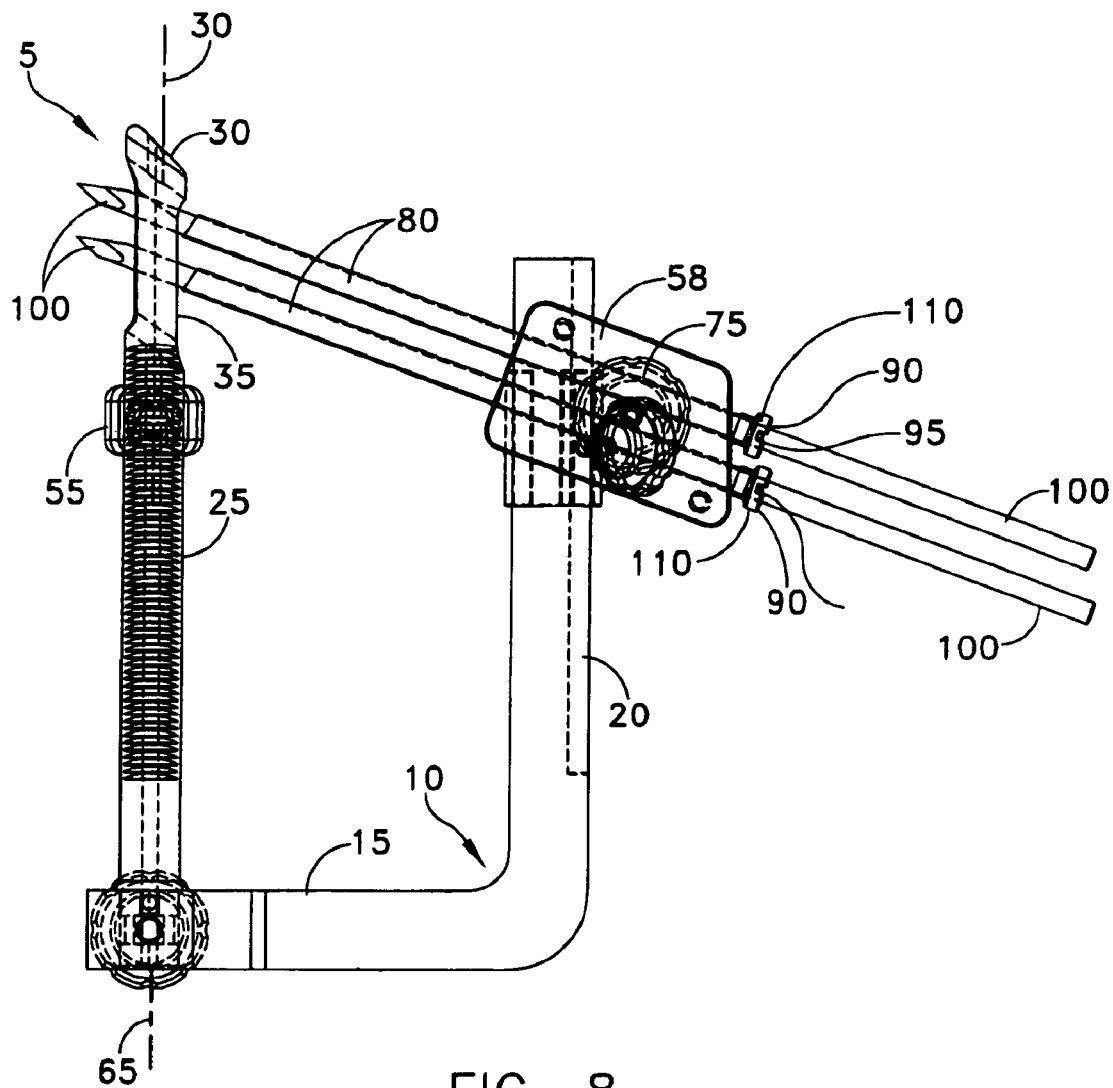
Figure 9:
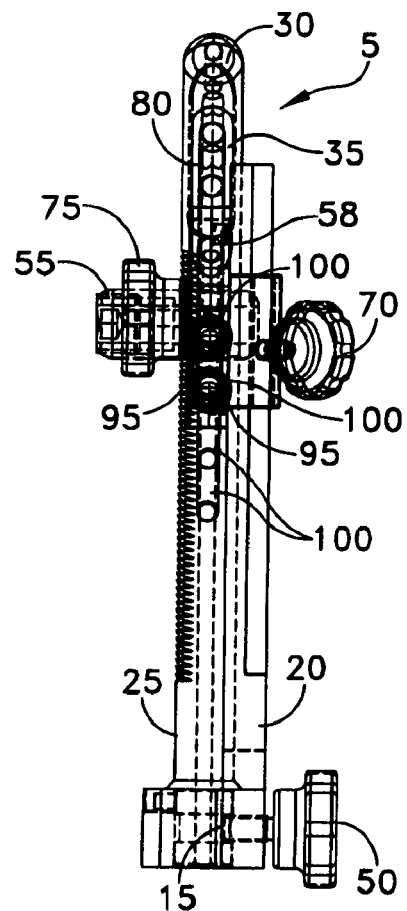
Figure 10:
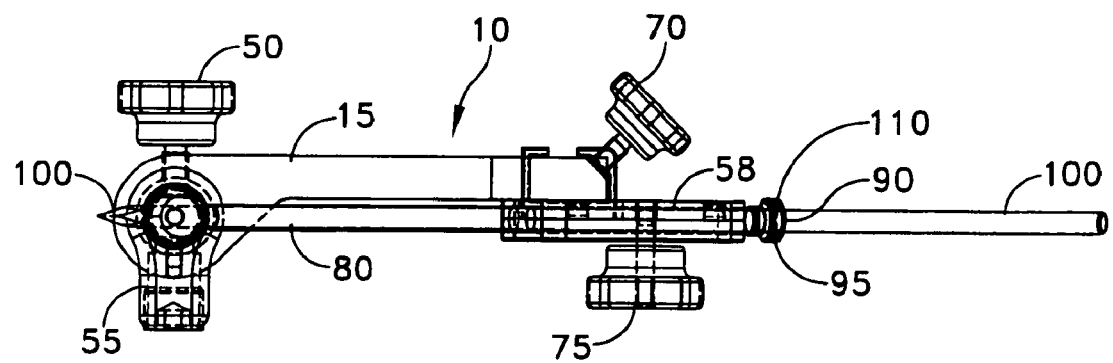
Figure 11:
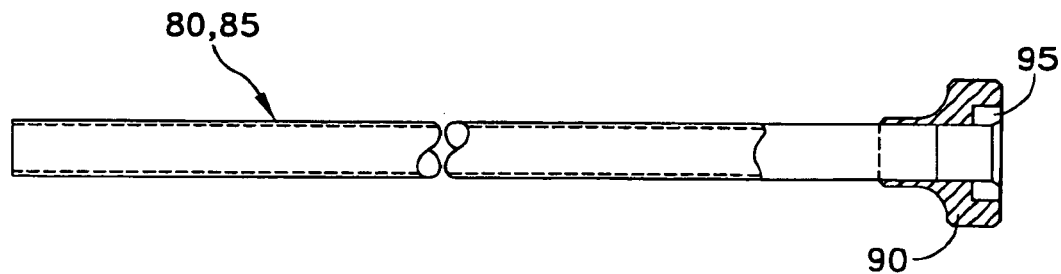
Figure 12:
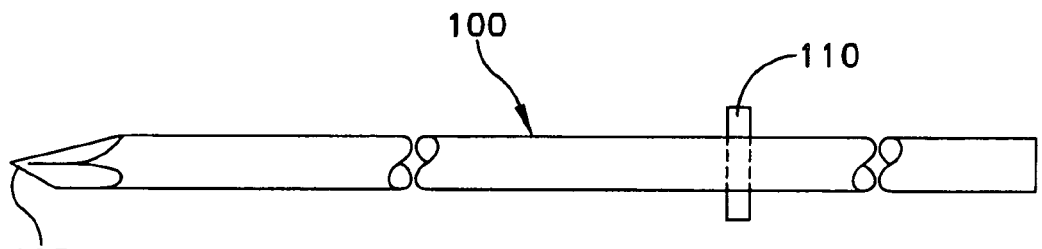
Figure 13:
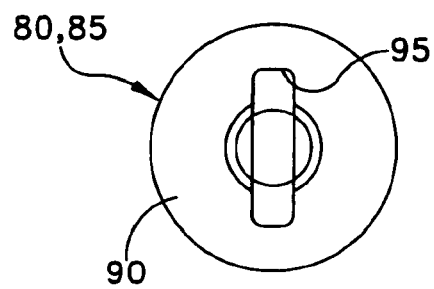

Looking first at FIGS. 1-10, there is shown a cross-pin guide assembly 5 for placement of at least one cross-pin (not shown in FIGS. 1-10) in a bone tunnel, such as the tibial tunnel of a knee joint. Cross-pin guide assembly 5 comprises an L-shaped member 10 having a base portion 15 and an arm portion 20. The arm portion 20 extends transversely to, and preferably is normal to, base portion 15.

Cross-pin guide assembly 5 further comprises a bone tunnel guide rod 25 which, adjacent to a first end 30 thereof, forms a diametrical, longitudinally-elongated passageway 35, and which, at a second end 40 thereof, is releasably connectable to base portion 15 of L-shaped member 10. In a preferred embodiment, bone tunnel guide rod 25 is cannulated along its axis 65 (see FIGS. 1-10) for placement on a guidewire (not shown in FIGS. 1-10). Bone tunnel guide rod 25 may be retained in a bore 45 formed in base portion 15 by a set screw 50. In an alternative embodiment, bone tunnel guide rod 25 may be fixedly connected to base portion 15.

Still looking at FIGS. 1-10, a movable element 55 is positioned on bone tunnel guide rod 25 between first end 30 and second end 40. Movable element 55 may be moved about on guide rod 25 so that the distance of movable element 55 from first end 30 may be selectively adjusted. Movable element 55 may also be secured to guide rod 25 at any of these longitudinal positions. In one preferred form of the invention, movable element 55 is movably secured to guide rod 25 using a ratchet system such as that shown in FIGS. 1-10.

The present invention may be practiced with cross-pins of any type, and is independent of the type of cross-pins used in a surgical procedure. Preferably, cross-pins of an absorbable nature are used in a given surgical procedure. Accordingly, the ACL reconstruction will hereinafter be discussed in the context of using absorbable cross-pins, and in the context of using preferred apparatus for deploying such absorbable cross-pins.

More particularly, in a preferred embodiment using absorbable cross-pins 255, 260 (FIG. 34), a trocar sleeve guide member 58 (FIGS. 1-10) is removably connectable to arm portion 20 of L-shaped member 10. Trocar sleeve guide member 58 is provided with bores 60 extending therethrough. Bores 60 intersect the longitudinal axis 65 of the bone tunnel guide rod 25. As such, at least one cross-pin is ultimately positioned in the tibia so as to pass through the tibial tunnel. More preferably, bores 60 are configured to intersect the longitudinal axis 65 of bone tunnel guide rod 25 just below the patient's tibial plateau. In this way, the at least one cross-pin will be deployed in the cortical portion of the tibia, adjacent to the tibial plateau, and at the region of greatest bone strength. A set screw 70 may be used to releasably retain trocar sleeve guide member 58 in position on arm portion 20. Alternatively, or in addition, arm portion 20 may be provided with stop means (not shown) for limiting movement of the trocar sleeve guide member 58 along arm portion 20. Trocar sleeve guide member 58 is preferably formed in two halves releasably held together by a set screw 75, whereby trocar sleeve guide member 58 can be detached from first and second trocar sleeves 80, 85 passing through bores 60, as will hereinafter be discussed.

First and second trocar sleeves 80, 85 (FIGS. 1-10 and 11-13) are slidably received by bores 60 (FIG. 1) such that sleeves 80, 85 are axially and rotatably movable in bores 60. Trocar sleeves 80, 85 are each provided with a collar portion 90 having a diagonally-extending slot 95 formed therein. Cross-pin guide assembly 5 also preferably includes one or more trocars 100 (FIGS. 1-10 and 11-13) for disposition in sleeves 80, 85. Each trocar 100 is provided with a sharp end 105 for penetration of bone. A transversely-extending pin 110 is provided near, but spaced from, the opposite end of trocar 100. Pin 110 is fixed in place and is received by the slot 95 of trocar sleeves 80, 85 such that axial (in a distal direction) and rotational movement of trocar 100 causes similar movement of sleeves 80, 85.

First and second absorbable rods 255, 260 (see FIG. 34), or rods of other types of known materials, are slidable through sleeves 80, 85, as will be further described hereinbelow.

In another preferred embodiment, guide member 58 is configured for the direct placement of cross-pins, without the use of trocar sleeves 80, 85 and trocars 100. In this case, the cross-pins are inserted through, and guided by, each of bores 60 in guide member 58.

Figure 14:
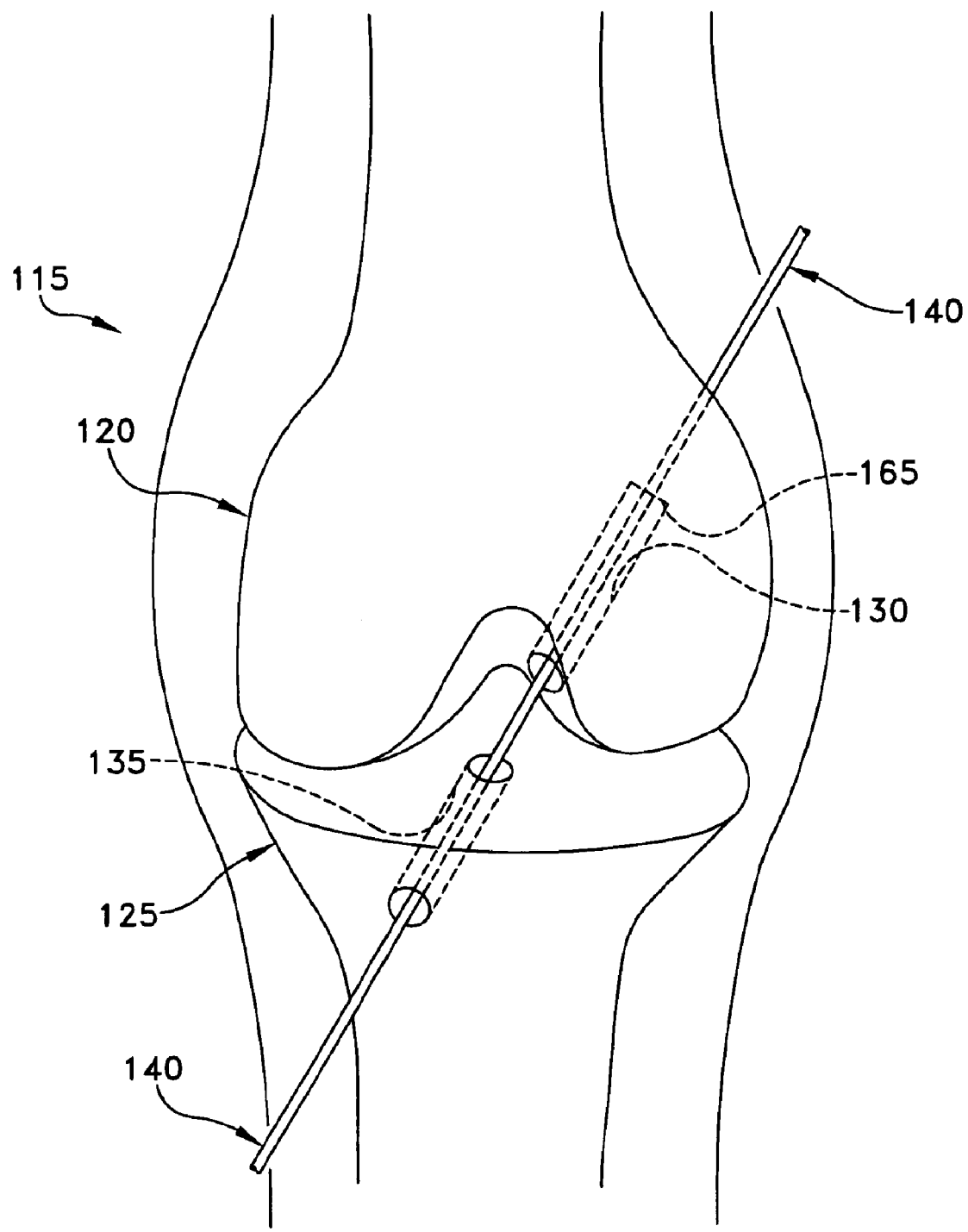
FIG. 14 is a diagrammatical view of a human knee joint and illustrative of a step in a method in which the cross-pin guide assembly of FIGS. 1-13 is used.

Referring now to FIG. 14, there is shown a human knee joint 115 including a femur 120 and a tibia 125. An appropriate femoral tunnel 130 and an appropriate tibial tunnel 135 are provided, as by means and methods well known in the art. A guidewire 140 extends through the tunnels 130, 135 as shown.

Figure 15:
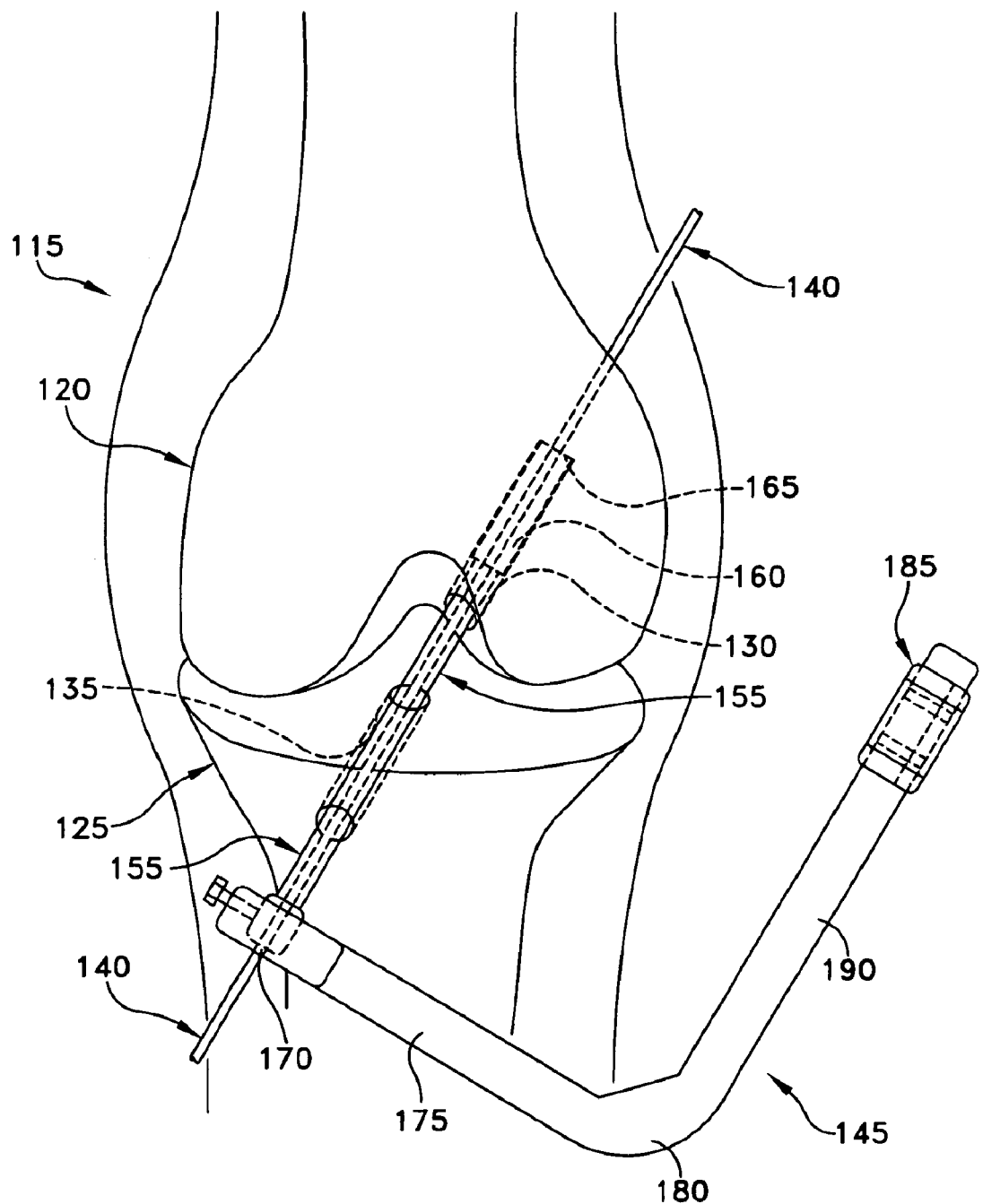
FIGS. 15-34 are diagrammatical views illustrating a ligament reconstruction procedure in which the cross-pin guide of FIGS. 1-13 is used.

Now looking at FIG. 15, a femoral cross-pinning rack assembly 145, or another similar system, is provided to position cross-pins 255, 260 (FIG. 30) across femoral tunnel 130. Using rack assembly 145, a cannulated sleeve 155 is loaded on guidewire 140, passed through tibial tunnel 135 and up into femoral tunnel 130 until the cannulated sleeve's head portion 160 (FIG. 15) engages in an annular shoulder 165 in femoral tunnel 130. Guidewire 140 extends through a bore 170 (FIG. 15) formed in a base portion 175 of L-shaped member 180. The cannulated sleeve's head portion 160 is preferably sized so as to form a snug fit in femoral tunnel 130. Cannulated sleeve 155 may be positioned in the bone tunnels 130, 135 and then connected to L-shaped member 180 or, more preferably, cannulated sleeve 155 may be first connected to L-shaped member 180 and then positioned in femoral tunnel 130 and tibial tunnel 135. Trocar sleeve guide member 185 (FIG. 15), if not already positioned on an arm portion 190, is then fixed to arm portion 190, as by a set screw (not shown).

Figure 16:
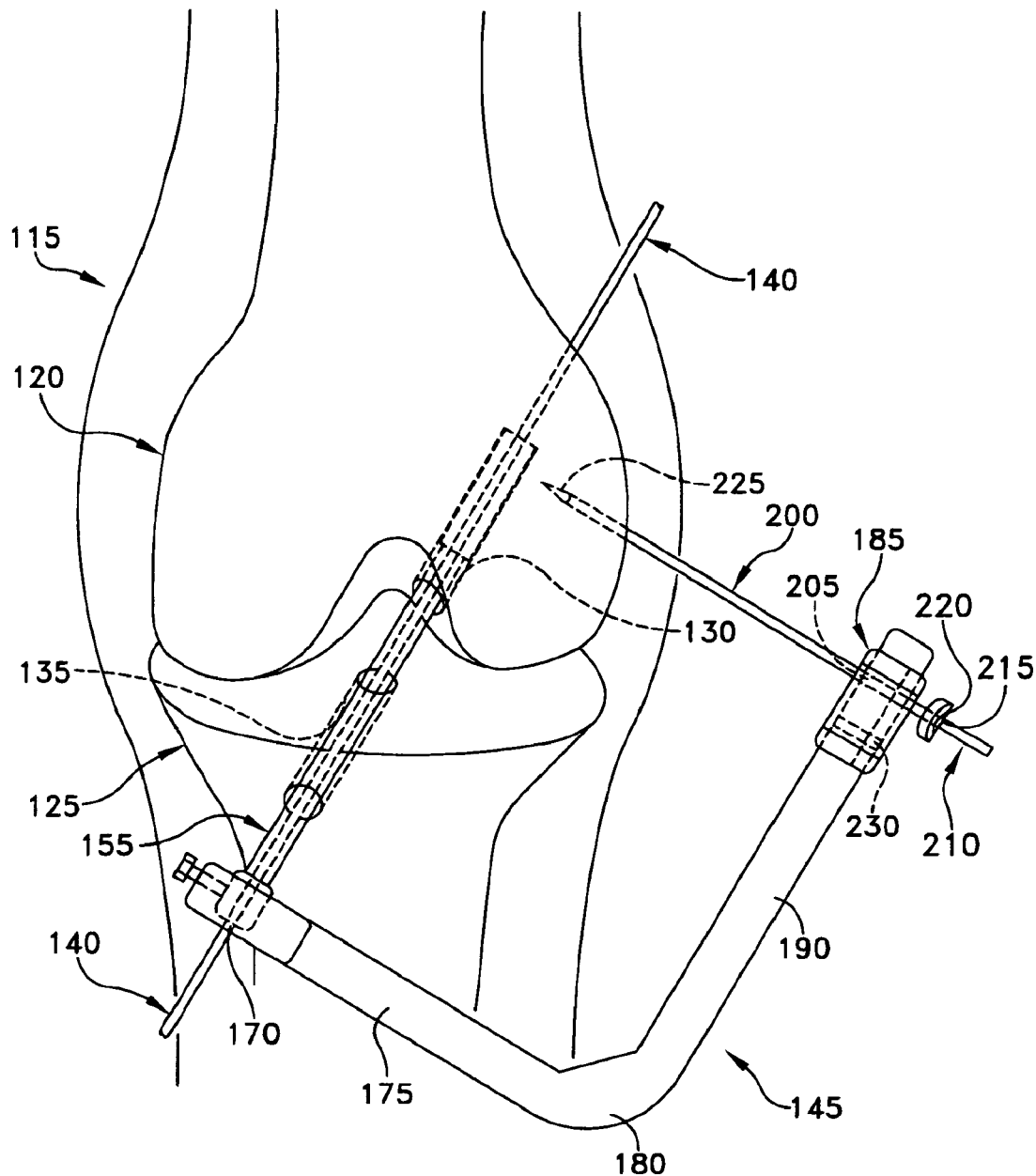

Now looking at FIG. 16, first trocar sleeve 200 is then inserted in a bore 205 of guide member 185 (FIG. 16), and trocar 210 is extended through sleeve 200 until pin 215 of trocar 210 is nestled in slot 220 of sleeve 200, with the trocar's sharp end 225 extending beyond the distal end of sleeve 200. Alternatively, trocar 210 may be mounted in first trocar sleeve 200 before the first trocar sleeve 200 is mounted in bore 205. In any case, the combination of trocar sleeve 200 and trocar 210 is then drilled, as a unit, into femur 120 toward, but stopped short of, the enlarged head portion. 160 of cannulated sleeve 155 (FIG. 16).

Figure 17:
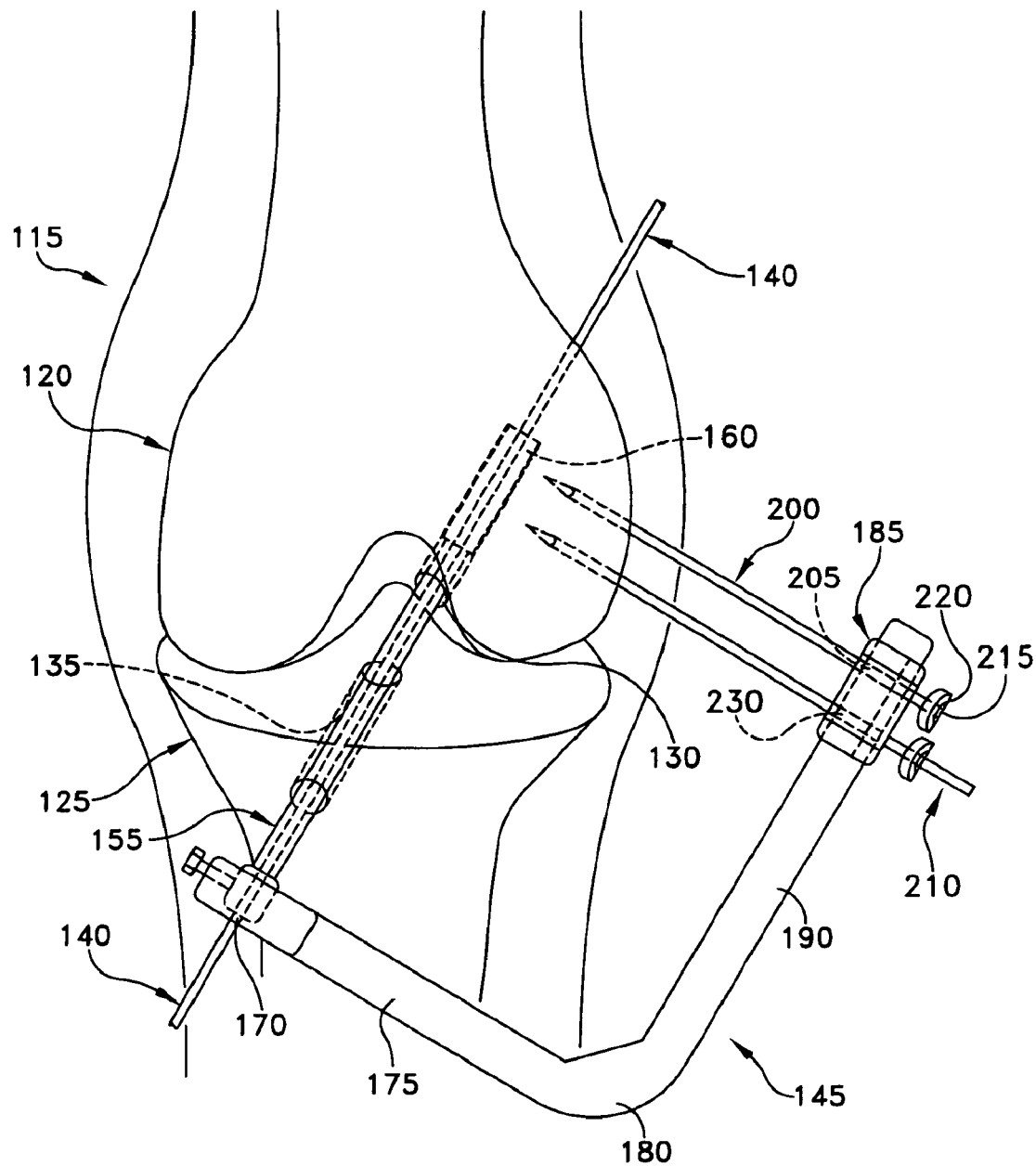
Figure 18:
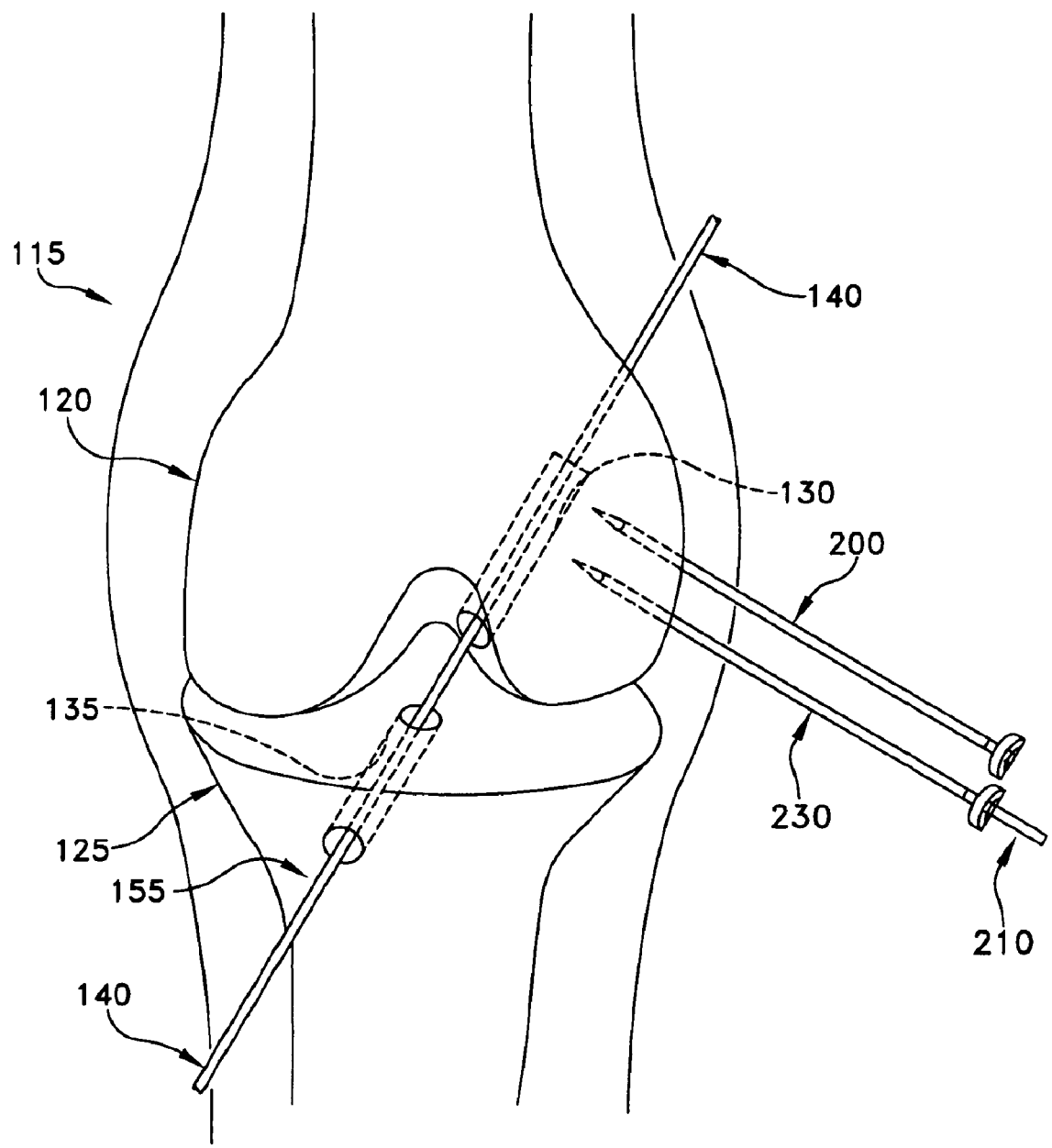

Trocar 210 may then be withdrawn from first trocar sleeve 200 and placed in a second trocar sleeve 230 (FIG. 17). Alternatively, a second trocar 210 may be provided for second trocar sleeve 230. In either case, the combination of trocar sleeve 230 and trocar 210 is then drilled, as a unit, into femur 120 toward, but again stopped short of, head portion 160 of cannulated sleeve 155 (FIG. 17). The rack's L-shaped member 180 may then be removed from the surgical site (FIG. 18). This may be accomplished by first loosening a set screw (not shown) to separate trocar sleeve guide member 185 into its two halves, whereby trocar sleeves 200, 230 will be freed from guide member 185, and then sliding cannulated sleeve 155 downward along guidewire 140 until the cannulated sleeve emerges from bone tunnels 130, 135. This procedure will leave trocar sleeves 200, 230 lodged in femur 120 (FIG. 18).

Figure 19:
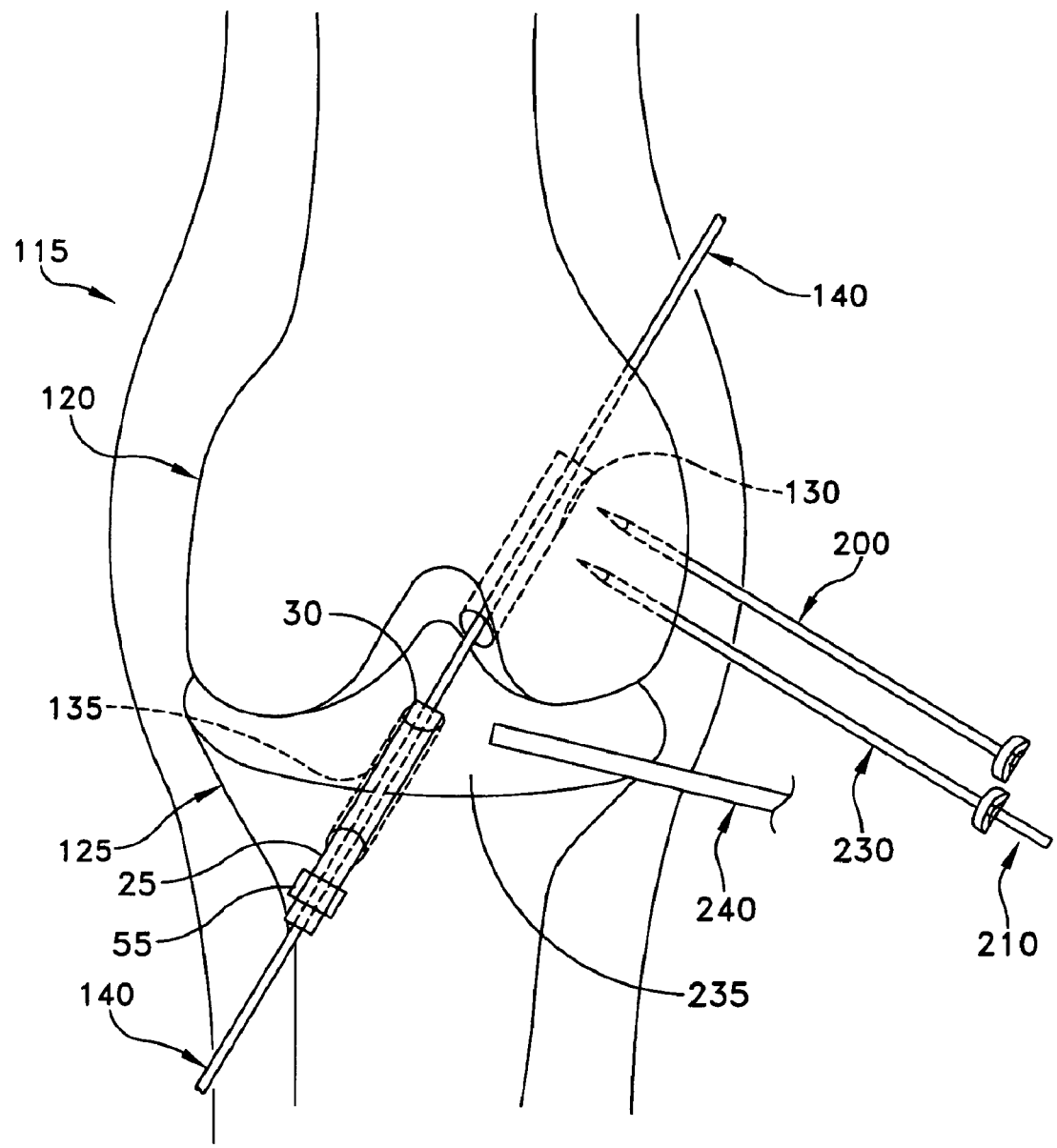

Referring now to FIG. 19, the bone tunnel guide rod 25 (FIGS. 1-10) is fed over guidewire 140 and up into tibial tunnel 135 until the guide rod's first end 30 is aligned with tibial plateau 235. An arthroscope 240 may be used to determine when the guide rod's first end 30 is aligned with tibial plateau 235.

Figure 20:
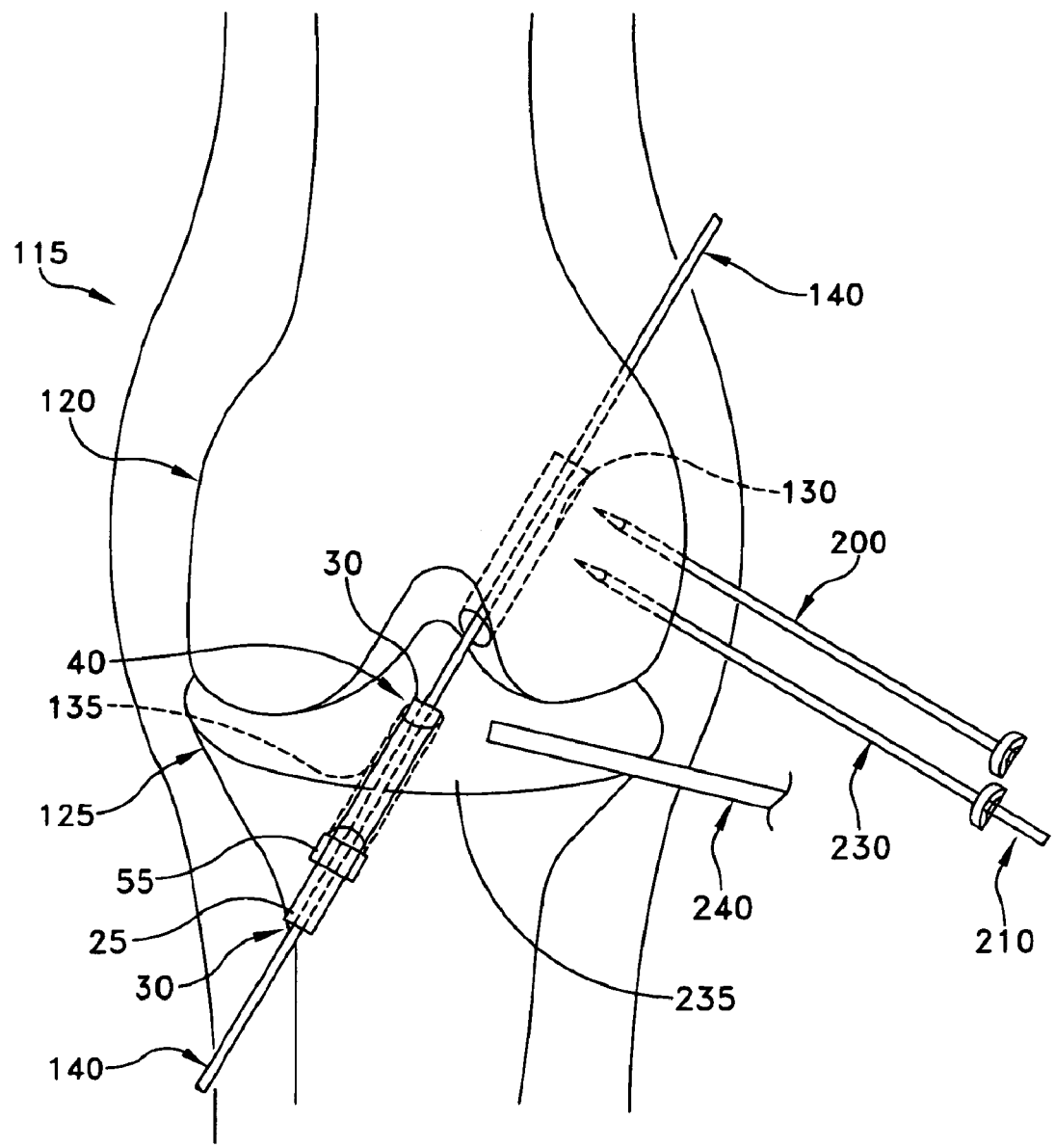

Referring now to FIG. 20, movable element 55 (FIGS. 1-10) is then moved along guide rod 25 toward the guide rod's first end 30 and tibia 125. When movable element 55 is positioned against tibia 125 (and the guide rod's first end 30 is positioned adjacent tibial plateau 235), movable element 55 is locked in position such that guide rod 25 cannot travel further into tibial tunnel 135. In this configuration, guide assembly 5 may be stabilized against tibia 125 by applying a distally-directed force to guide rod 25, with movable element 55 maintaining the position of the guide rod relative to tibia 125.

Figure 21:
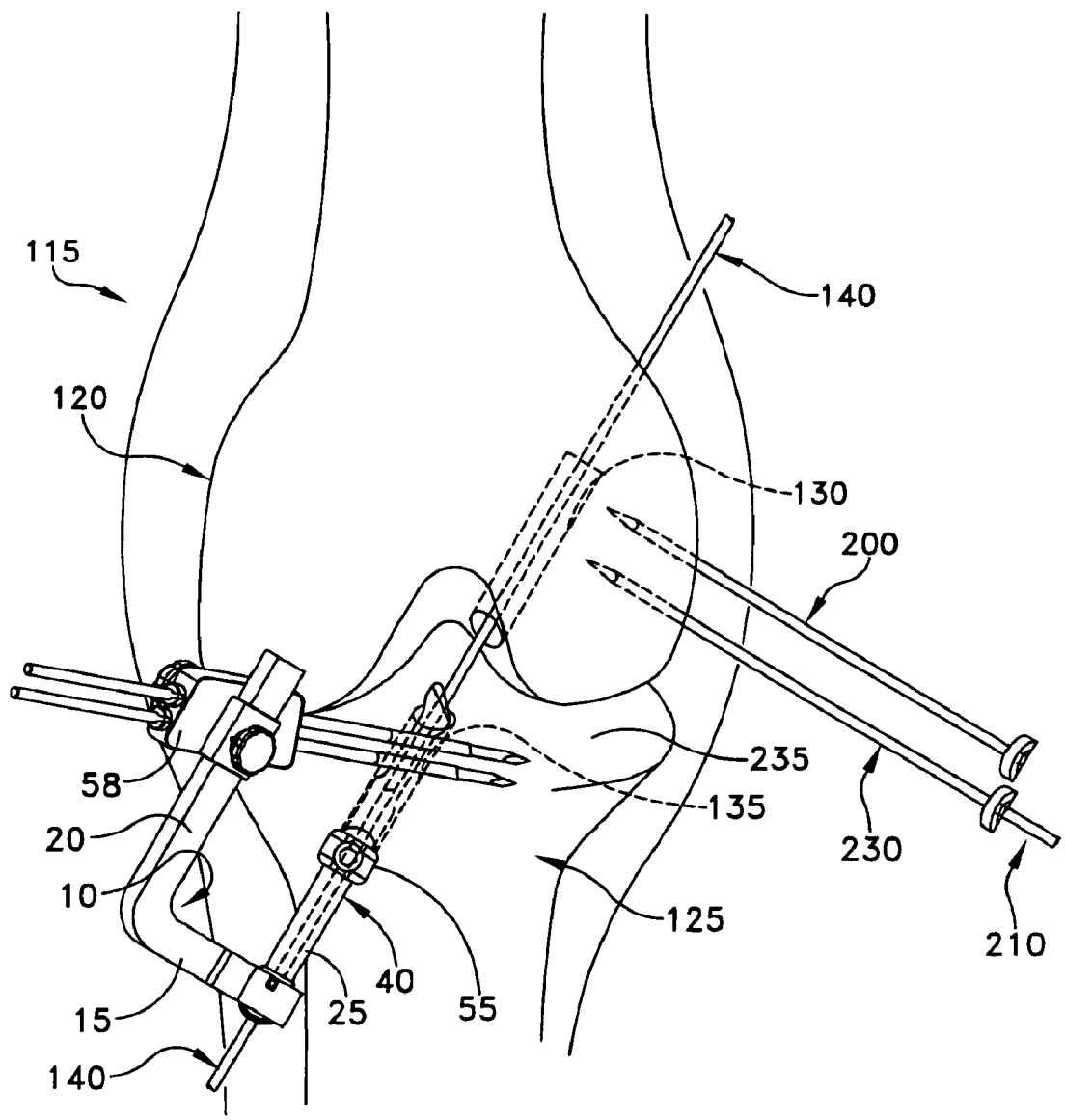
Figure 34:
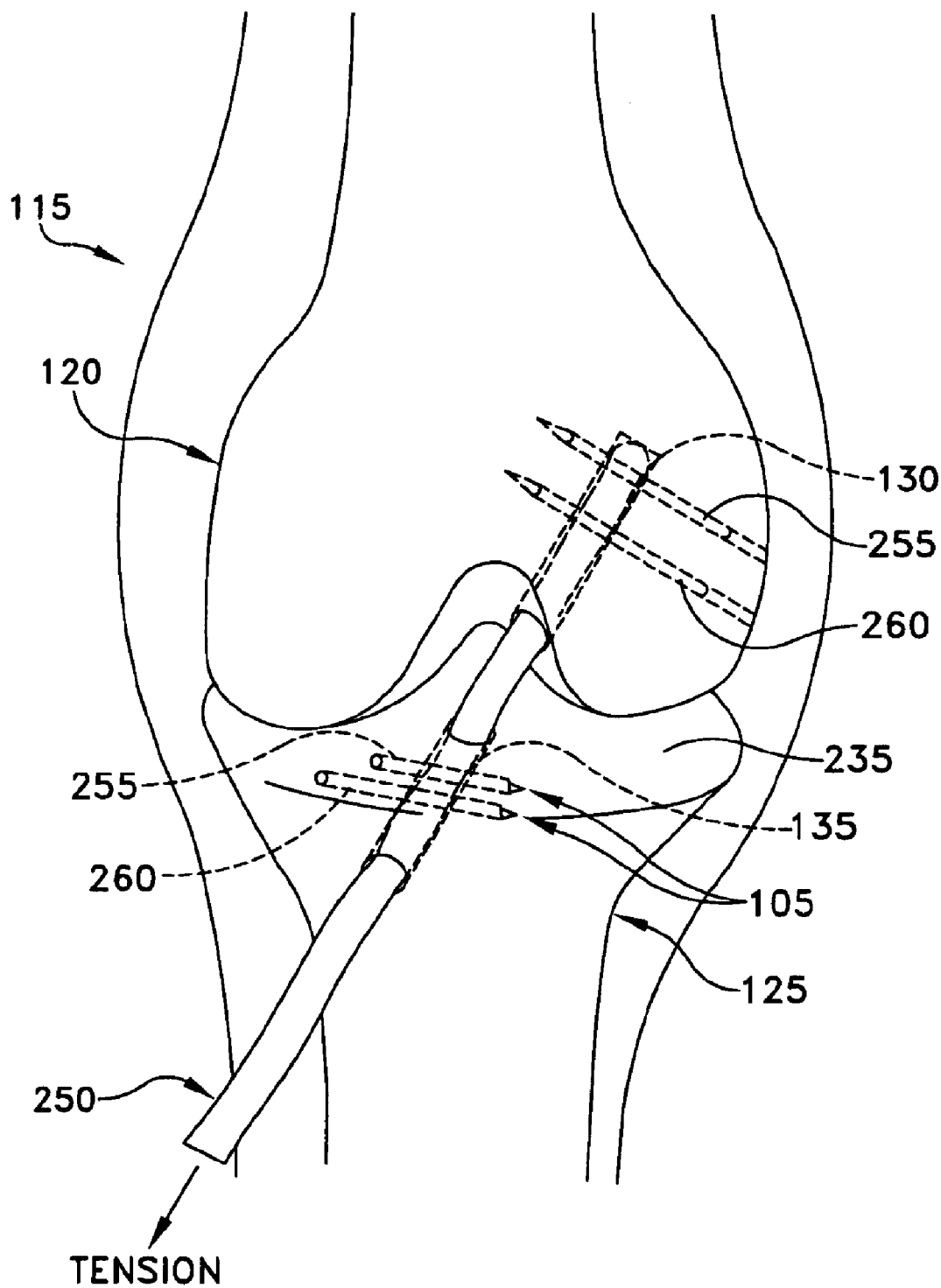
Figure 35:
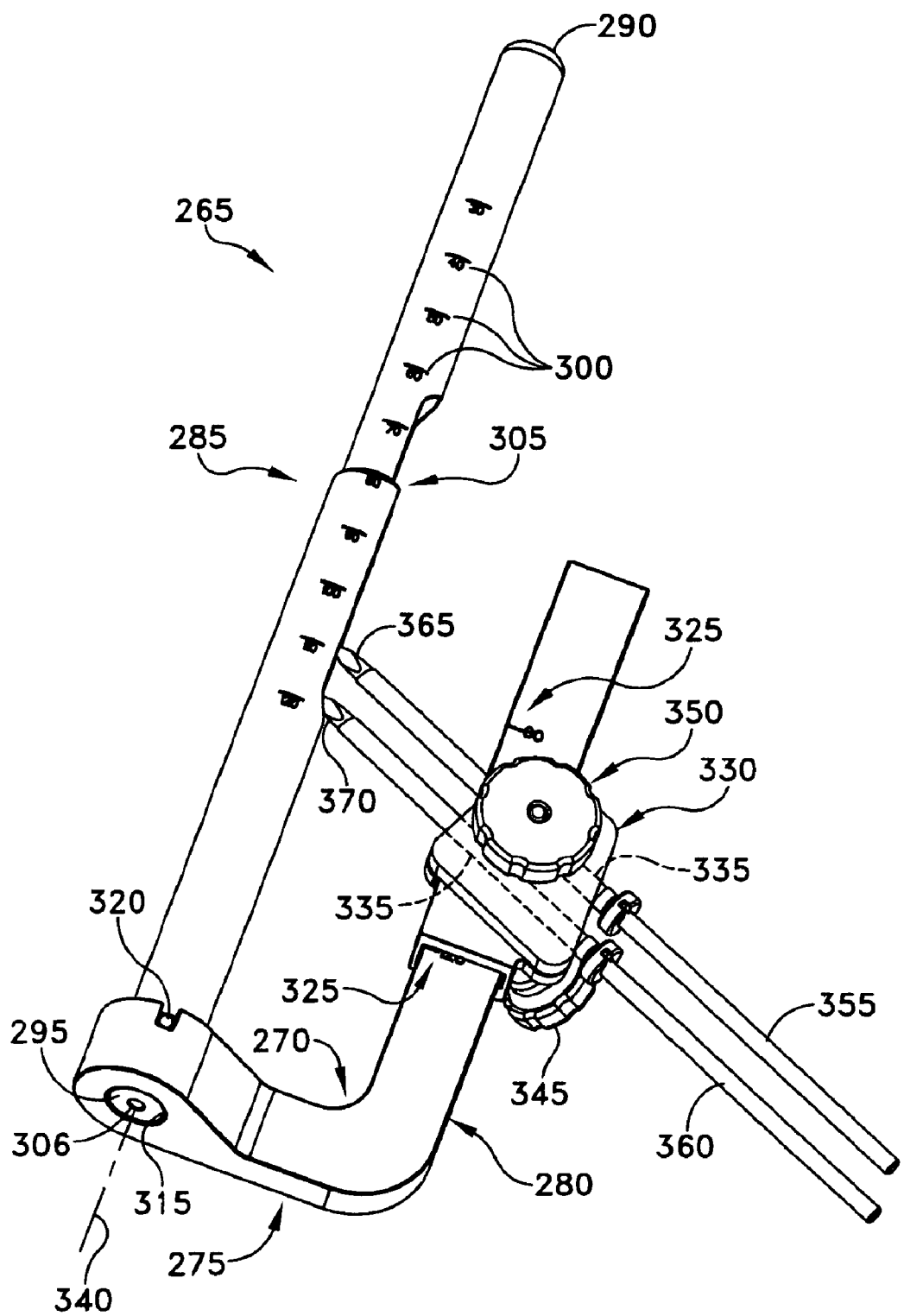
FIGS. 35-38 are various views of another form of a cross-pin guide assembly for use in cross-pinning a graft in a tibial tunnel, illustrative of another preferred embodiment of the present invention.
Figure 36:
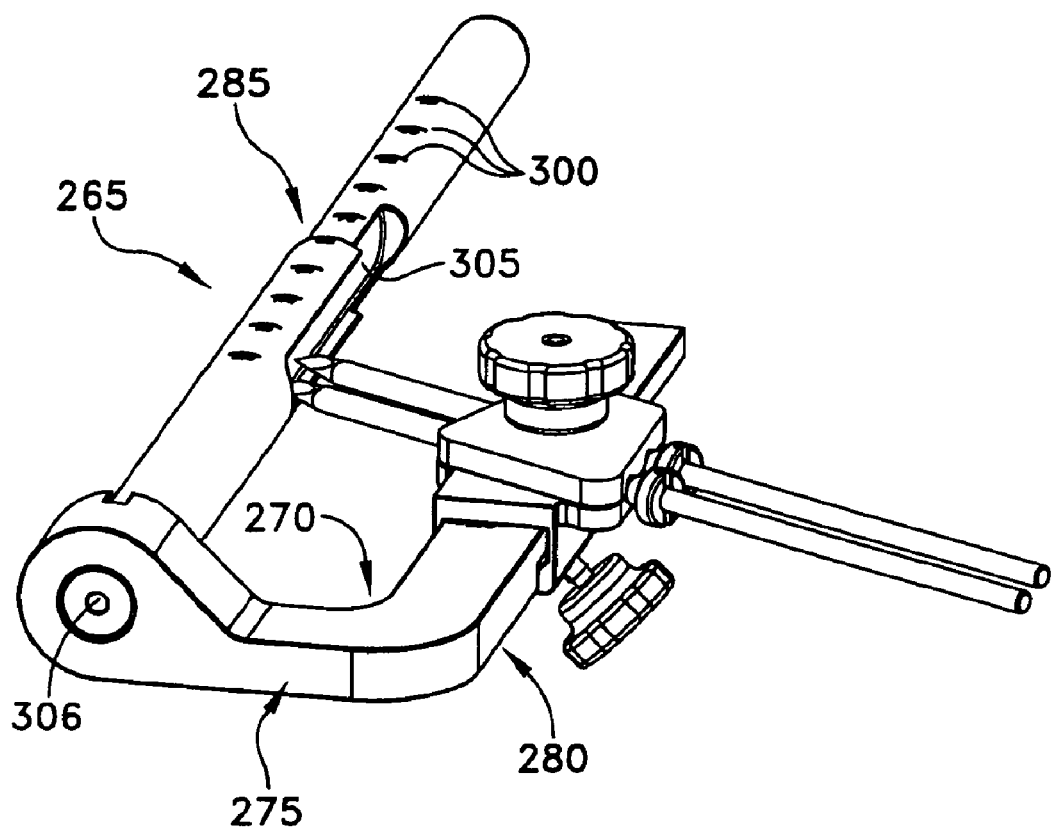
Figure 37:
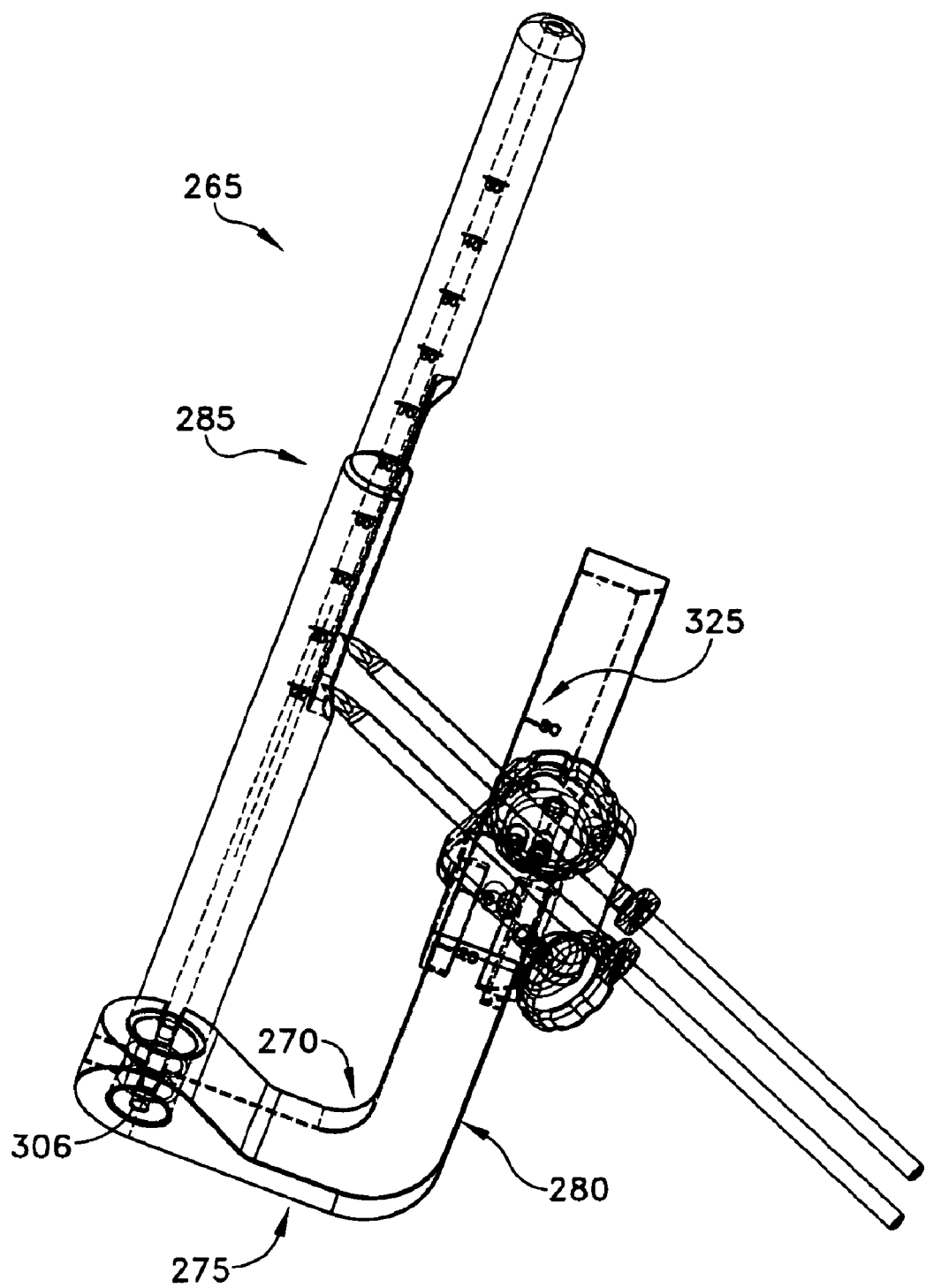
Figure 38:
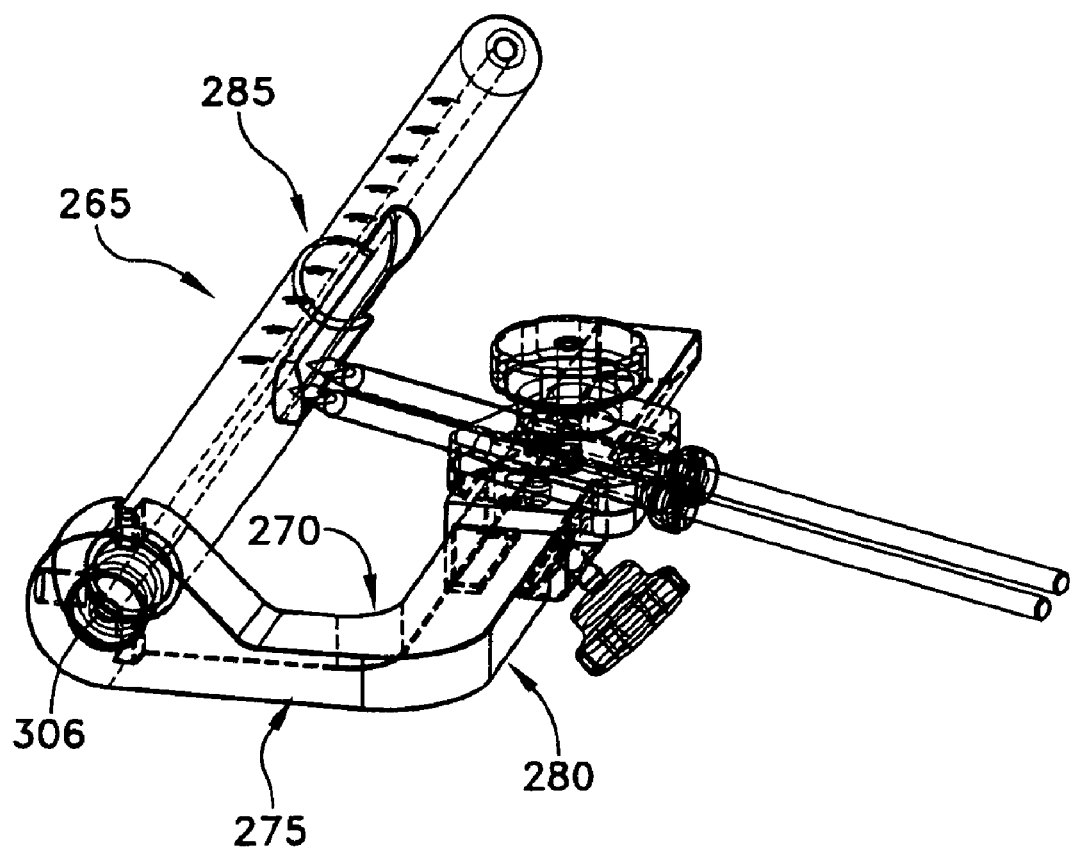

Now looking at FIG. 21, bone tunnel guide rod 25 is shown connected to L-shaped member 10 and positioned in tibial tunnel 135. In one embodiment, bone tunnel guide rod 25 may be first connected to L-shaped member 10 and then positioned in tibial tunnel 135. Alternatively, in a preferred embodiment, bone tunnel guide rod 25 is first positioned in tibia tunnel 135 and then connected to L-shaped member 10. In either case, movable element 55 properly locates bone tunnel guide rod 25 relative to tibia 125 so that the guide rod's first end 30 is aligned with tibial plateau 235. Trocar sleeve guide member 58 (FIGS. 1-10), if not already positioned on arm portion 20, is then fixed to arm portion 20, such as by set screw 50 (FIGS. 1-10). Guide assembly 5 has a geometry such that when first end 30 of bone tunnel guide rod 25 is positioned in tibial tunnel 135, and movable element 55 is in engagement with the front surface of tibia 125, the cross-pins 255, 260 (FIG. 34) will be directed with a desired orientation within the tibial bone and, more preferably, through the strong cortical bone located just below the tibial plateau 235 (FIG. 34).

Figure 22:
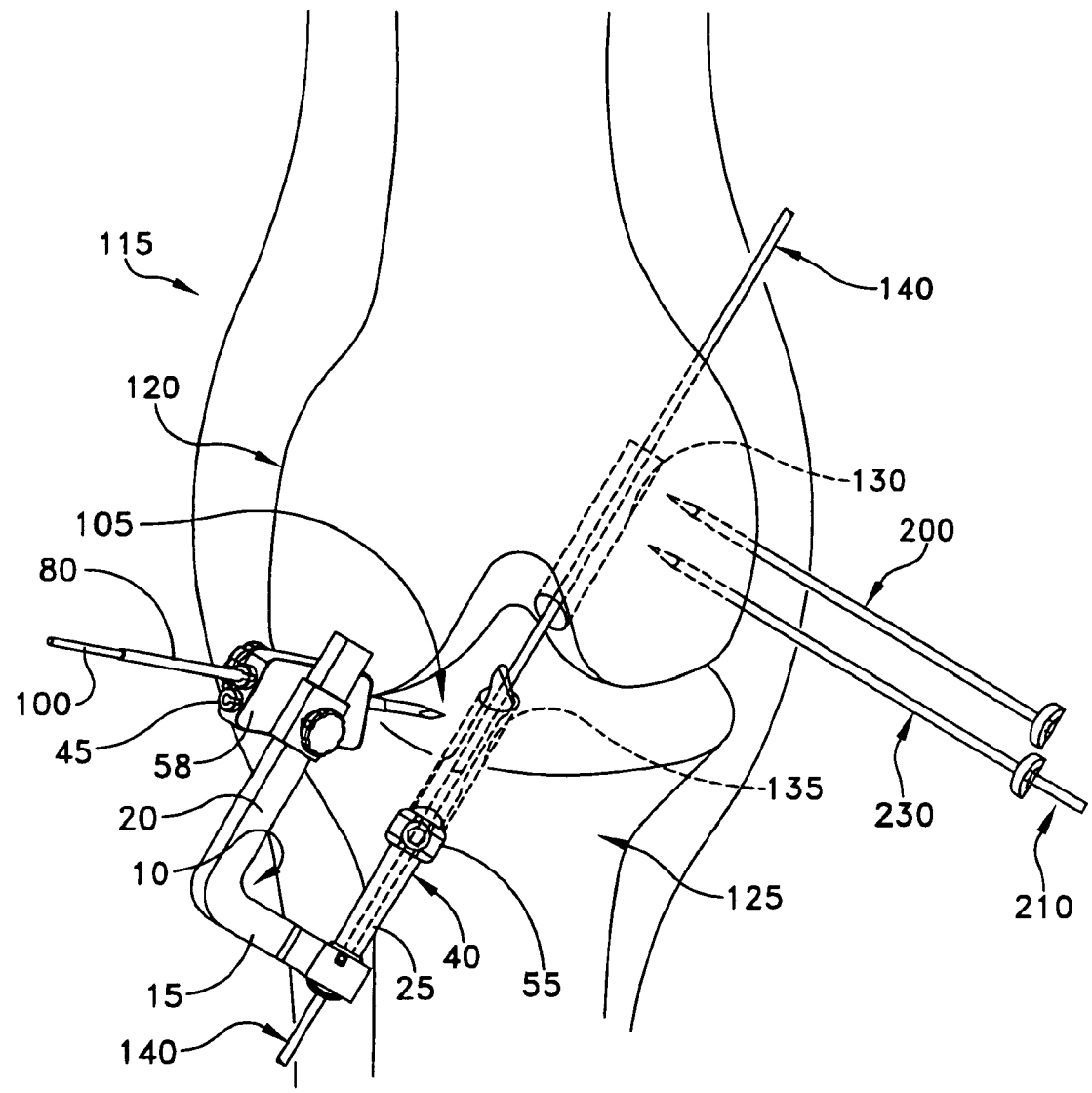

Now referring to FIG. 22, first trocar sleeve 80 is then inserted in bore 60 of guide member 58, and trocar 100 is extended through sleeve 80, with the trocar's sharp end 105 extending beyond the distal end of sleeve 80. Alternatively, trocar 100 may be mounted in first trocar sleeve 80 before first trocar sleeve 80 is mounted in the guide member's bore 60. In either case, the combination of trocar sleeve 80 and trocar 100 is then drilled, as a unit, into tibia 125 toward, but stopped short of, the guide rod's passage 35 (FIG. 22).

Figure 23:
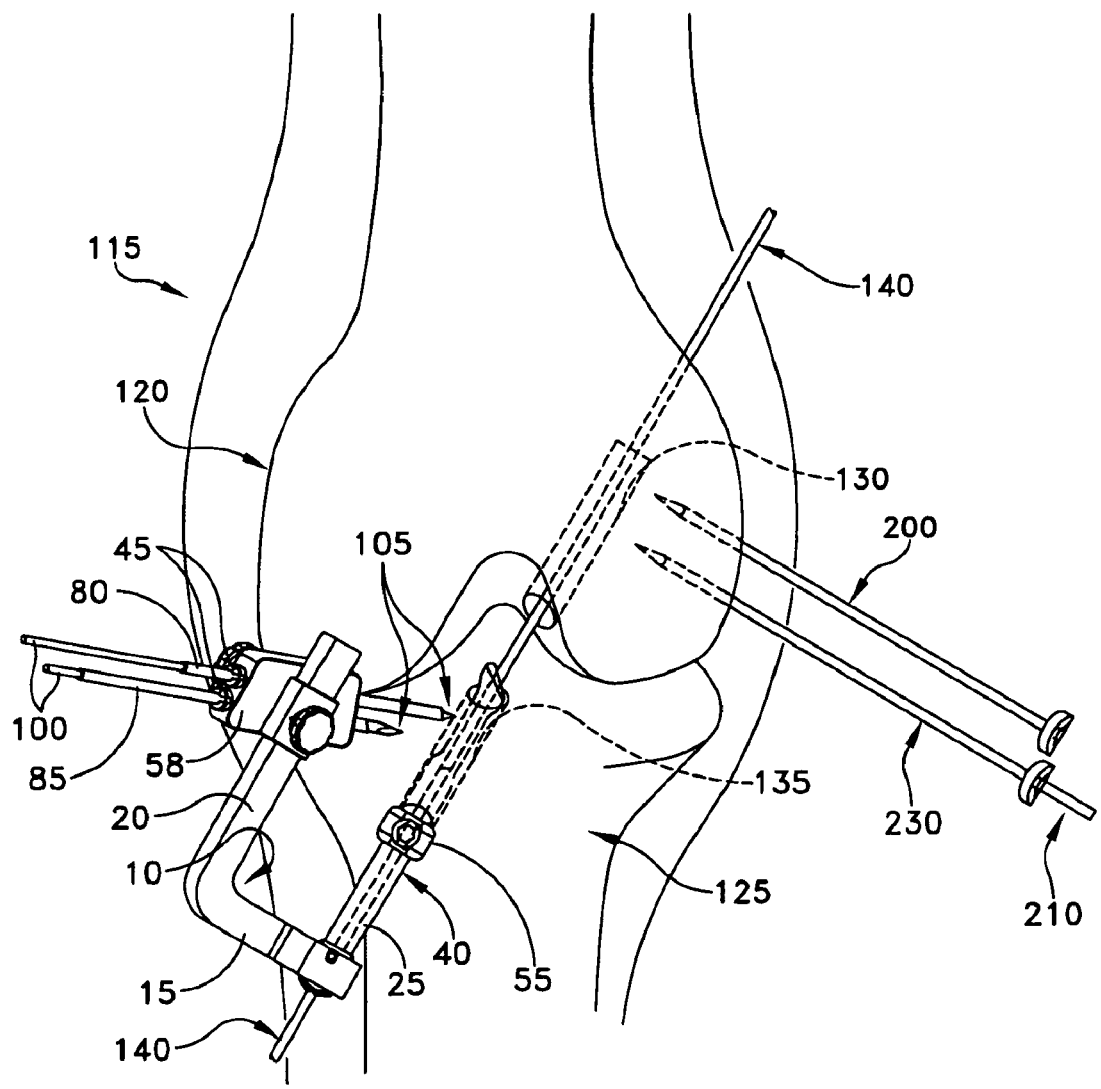
Figure 24:
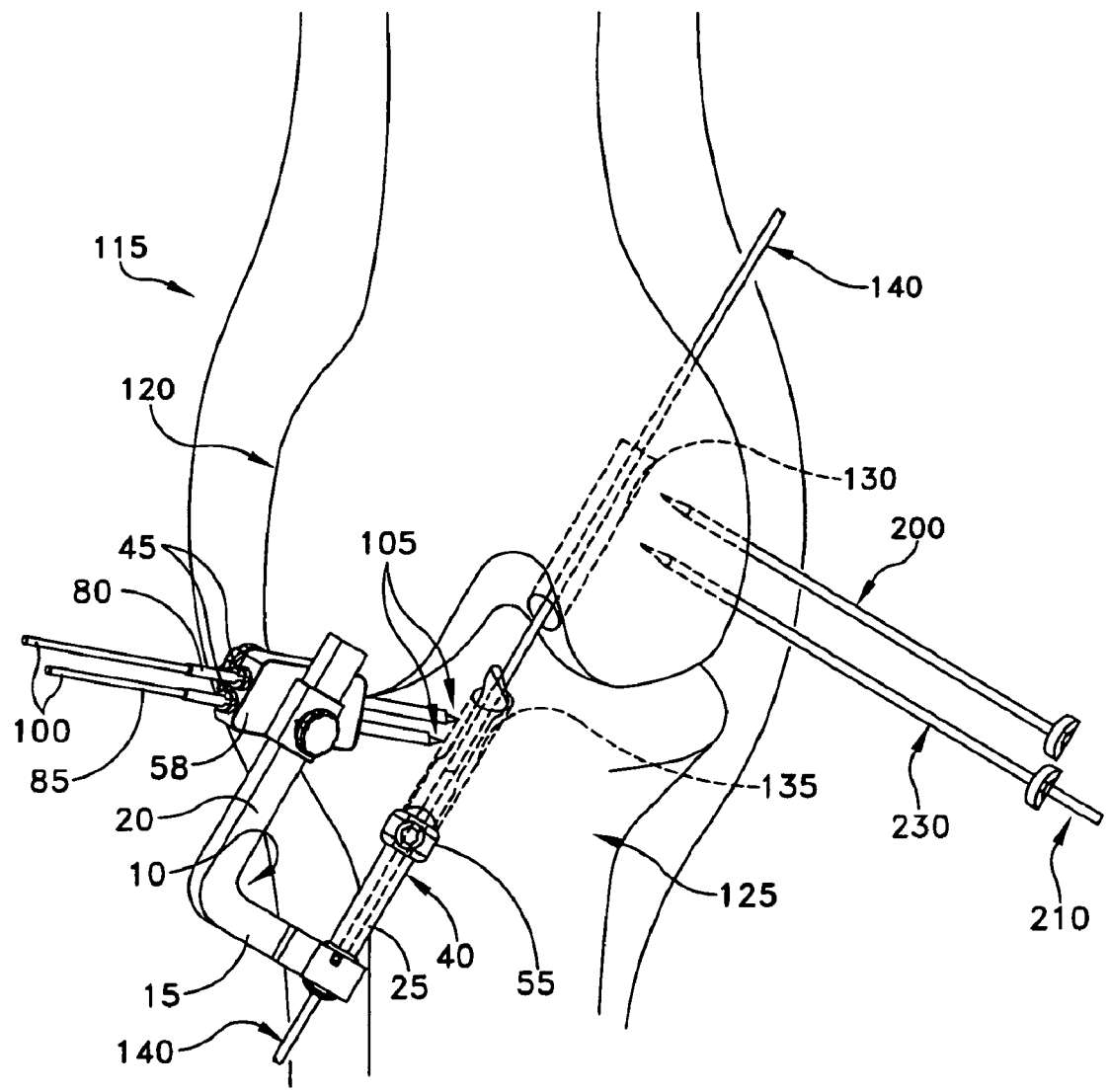

Trocar 100 may then be withdrawn from first trocar sleeve 80 and placed in second trocar sleeve 85. Alternatively a second trocar 100 may be provided for second trocar sleeve 85. In either case, the combination of trocar sleeve 85 and trocar 100 is then drilled (FIG. 23) as a unit into tibia 125 toward, but stopped short of, the guide rod (FIG. 24).

Figure 25:
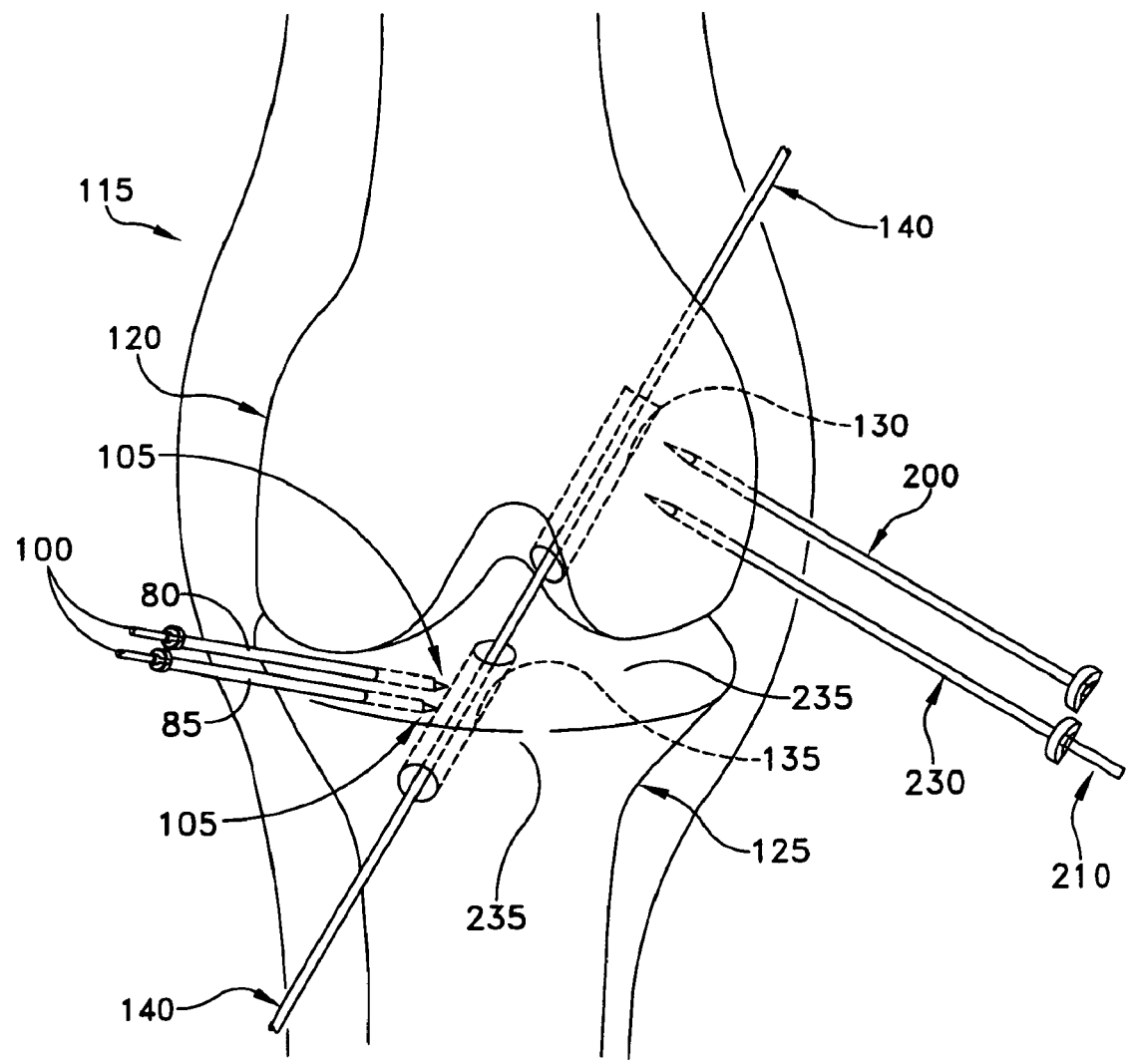

The guide assembly's L-shaped member 10 may then be removed from the surgical site. This may be accomplished by first loosening set screw 75 (FIGS. 1-10) so as to separate trocar sleeve guide member 58 into its two halves, whereby trocar sleeves 80, 85 will be freed from guide member 58, and then sliding bone tunnel guide rod 25 downward along guidewire 140 until the guide rod 25 emerges from tibial bone tunnel 135. This procedure will leave trocar sleeves 80, 85 lodged in tibia 125 (FIG. 25).

Significantly, due to the geometry of guide assembly 5, trocar sleeves 80, 85 (and hence cross-pins 255, 260) will be directed into the strong cortical bone located just beneath tibial plateau 235.

Figure 26:
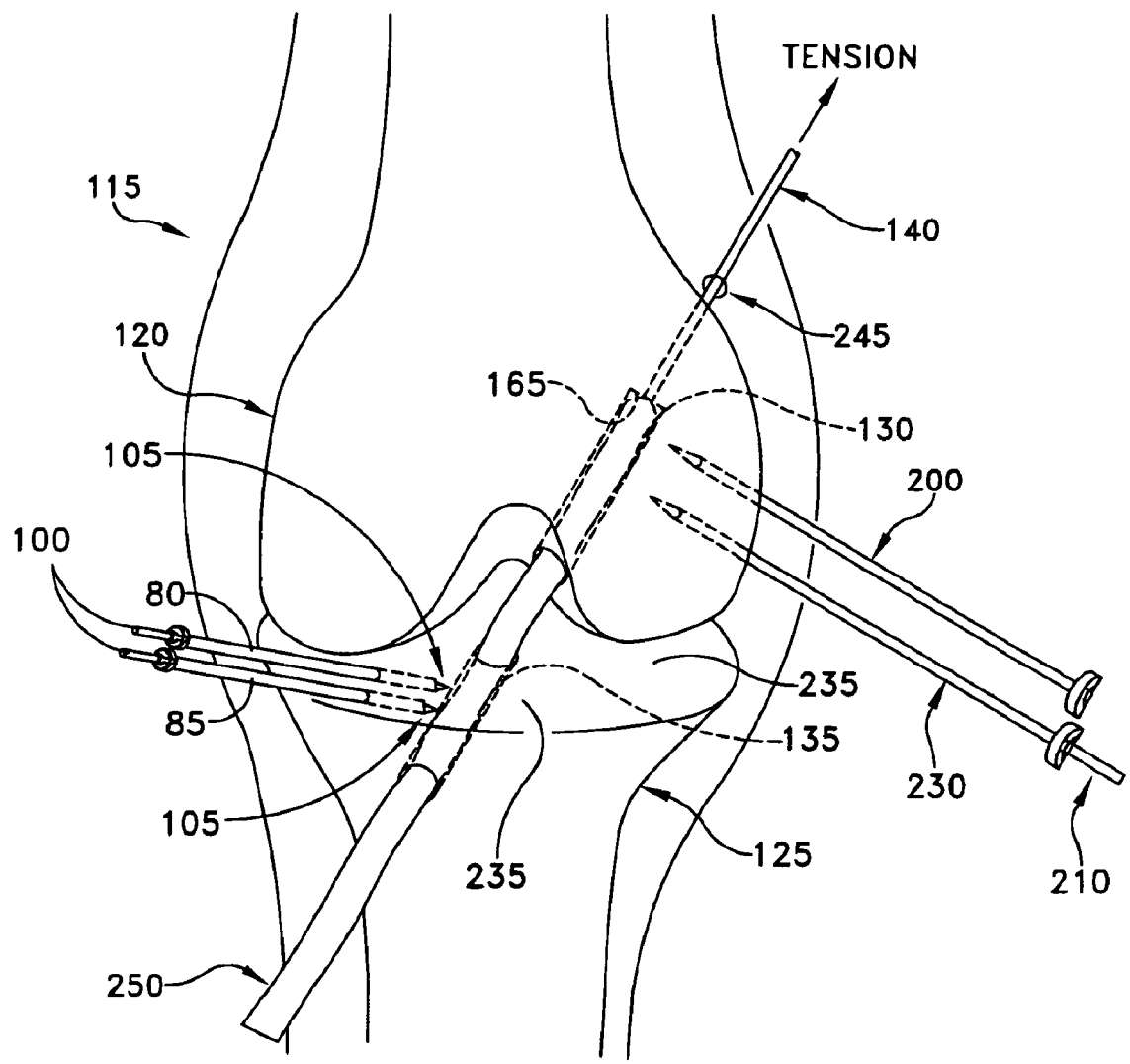

Guidewire 140 is then used to pull a suture 245, which is attached to a craft ligament 250 (including, but not limited to, soft tissue grafts and bone block grafts) up through tibial tunnel 135 and into femoral tunnel 130, until graft ligament 250 engages the annular shoulder 165 in femoral tunnel 130 (FIG. 26). Guidewire 140 may be provided with an eyelet (not shown) adjacent to its proximal end so as to facilitate this procedure. Graft ligament 250 can then be held in this position by maintaining tension on the portion of suture 245 emerging from the top of femur 120.

Figure 27:
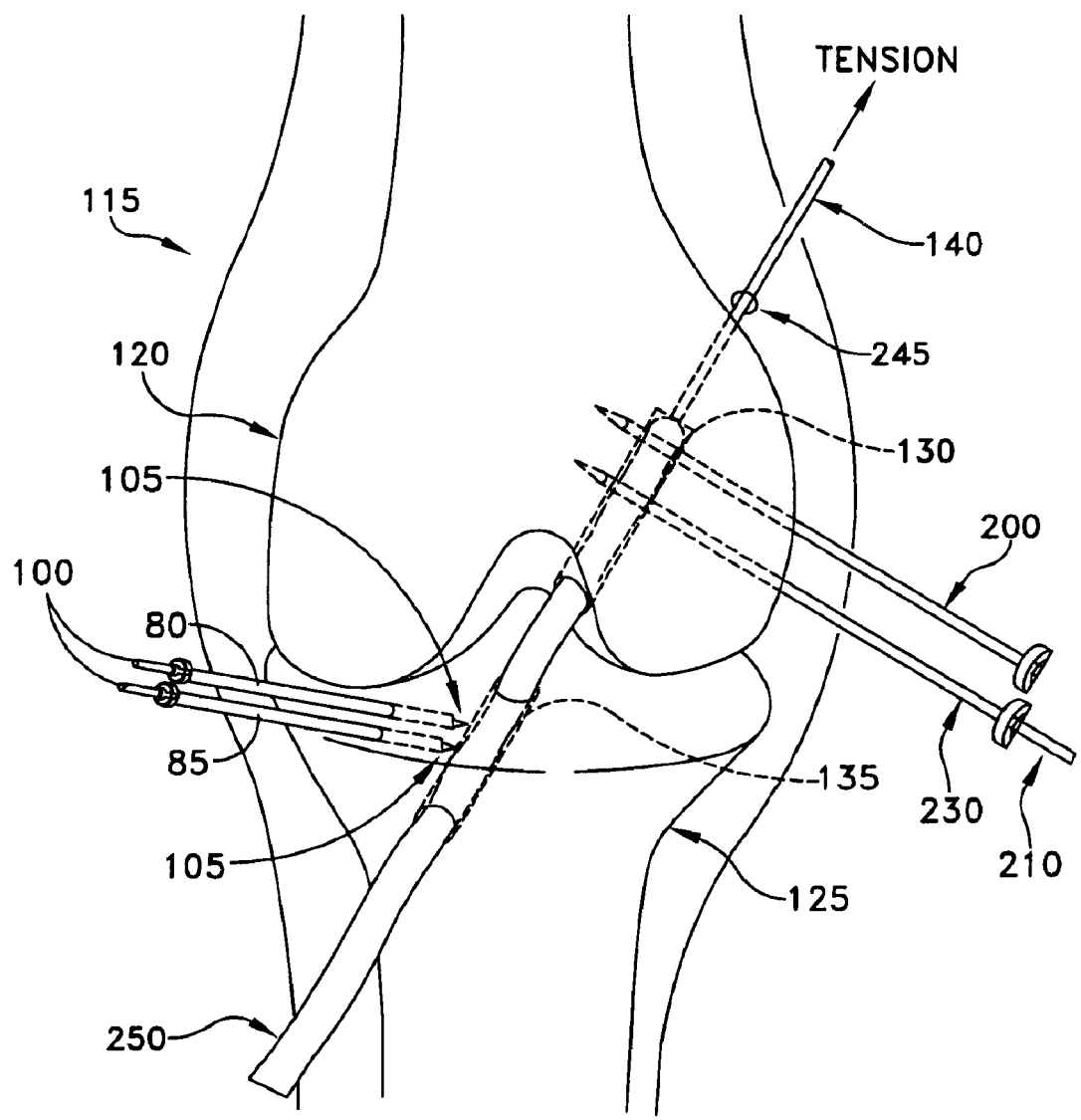
Figure 28:
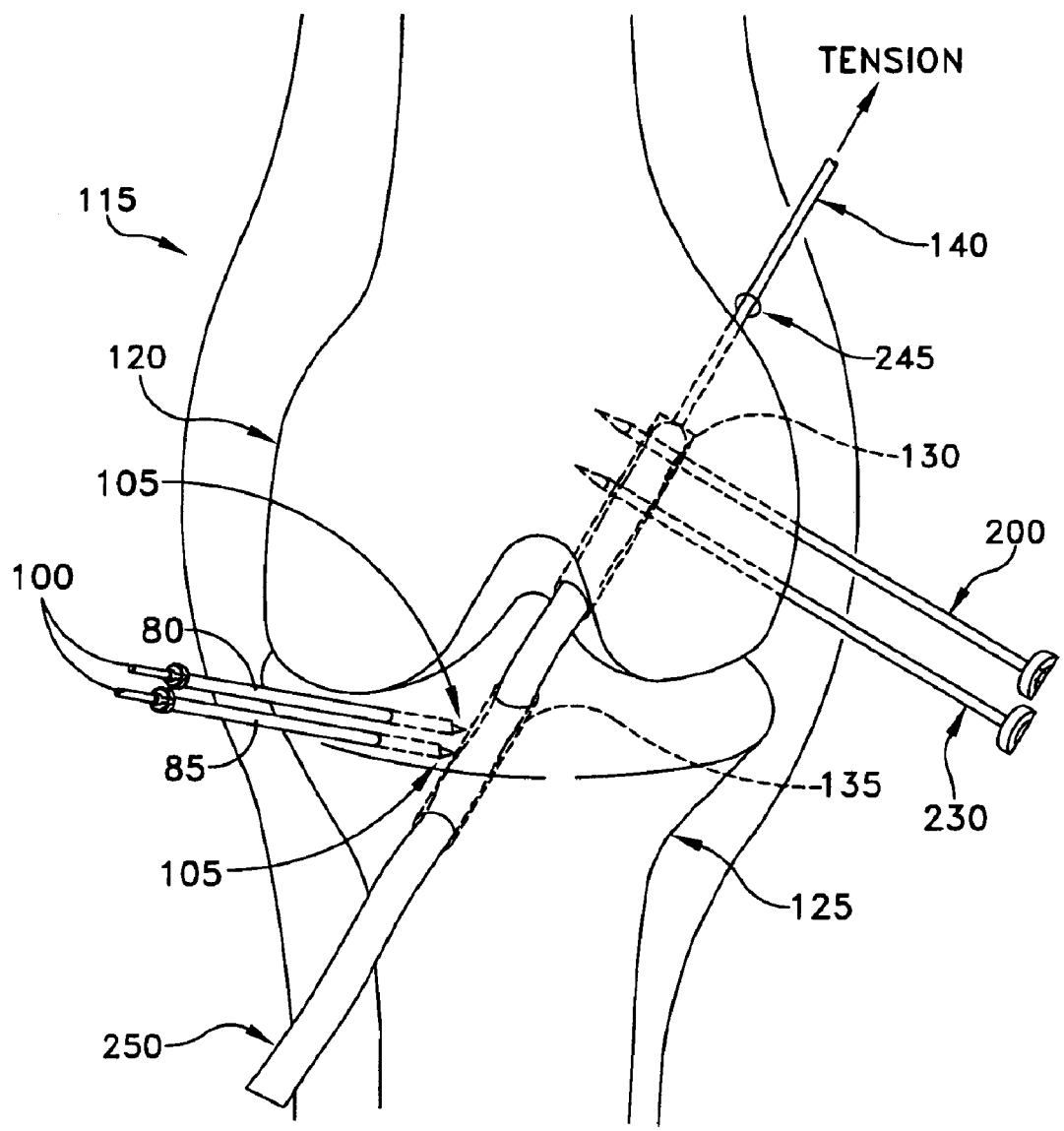
Figure 29:
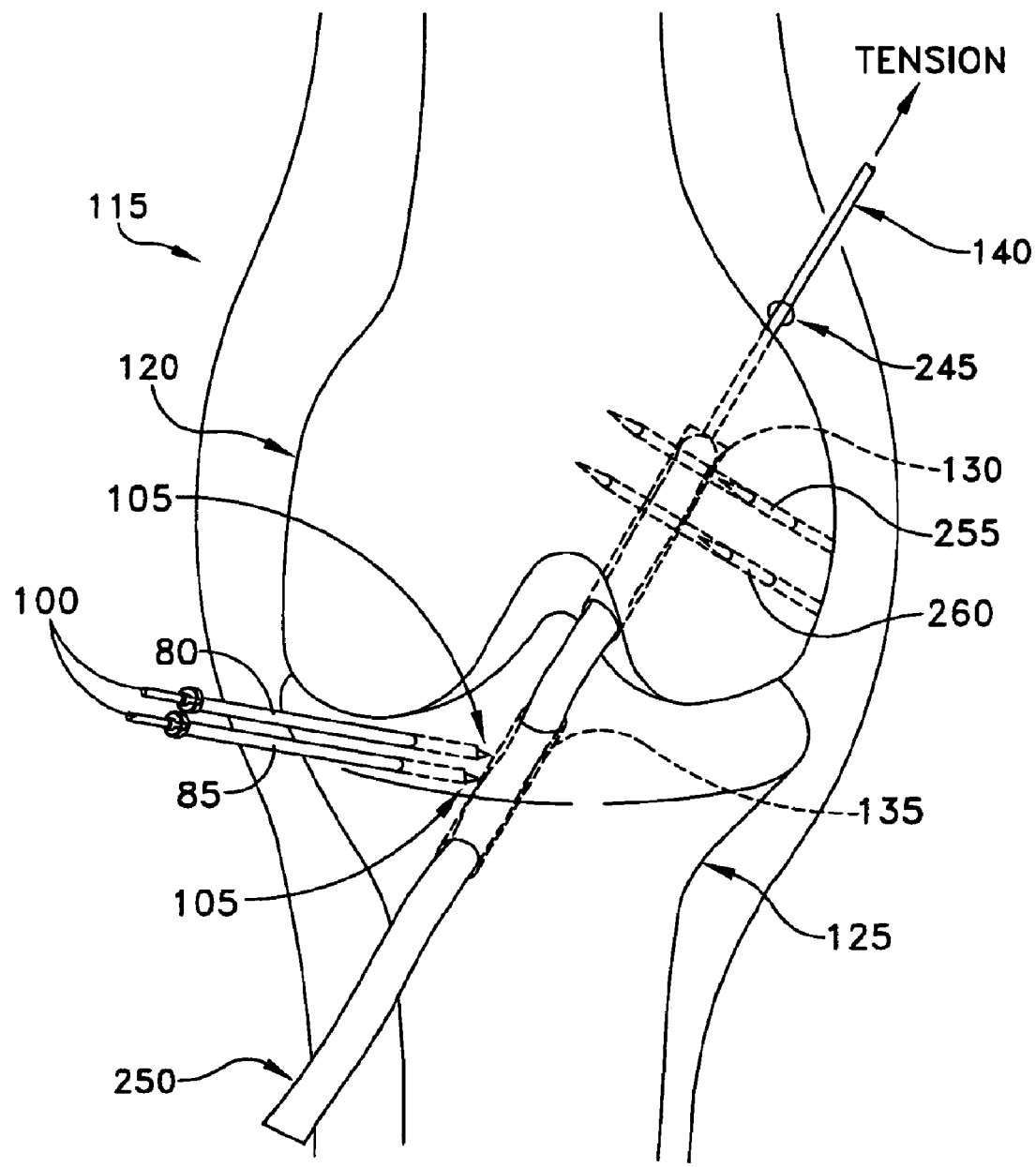

Trocar 210 may then be removed from second trocar sleeve 230, placed in first trocar sleeve 200, and then sleeve 200 and trocar 210 drilled through the distal end of graft ligament 250, as shown in FIG. 27. Trocar 210 may then be removed from sleeve 200, placed in second sleeve 230, and second sleeve 230 and trocar 210 drilled through the distal end of graft ligament 250, as also shown in FIG. 27. The trocar 210 (or trocars 210 if more than one trocar is used) may then be withdrawn from sleeves 200, 230 (FIG. 28). A first absorbable rod 255 (FIG. 29) is then deployed, by sliding rod 255 through trocar sleeve 200, into a position extending through ligament 250. Sleeve 200 may then be withdrawn from ligament 250 and femur 120, leaving first absorbable rod 255 in place in femur 120 and extending through ligament 250. Similarly, second absorbable rod 260 may be slid into place through sleeve 230. Sleeve 230 is then removed, leaving second absorbable rod 260, along with first absorbable rod 255, extending through ligament 250 so as to lock ligament 250 in place in femoral tunnel 130, as shown in FIG. 29.

Figure 30:
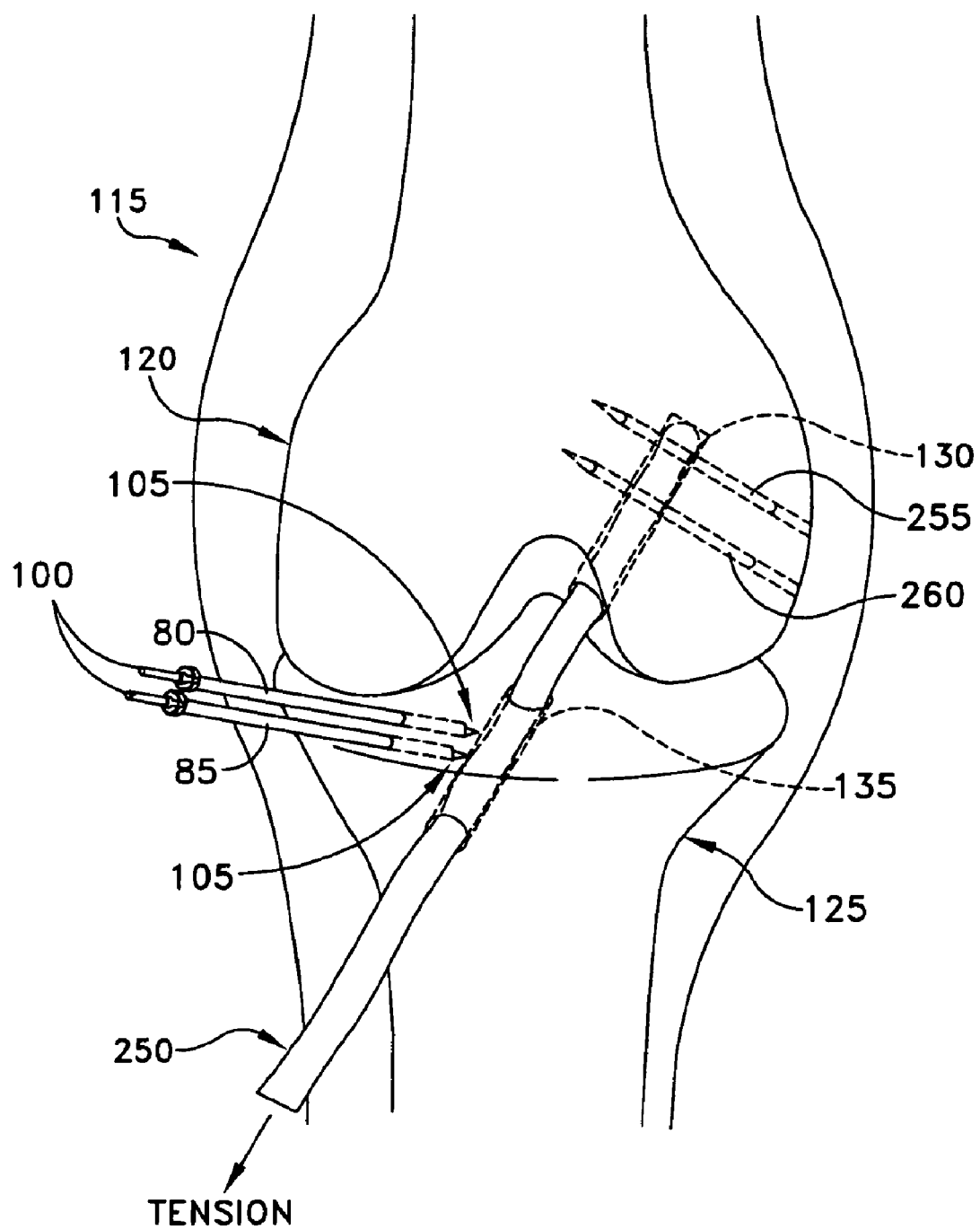

Looking next at FIG. 30, graft ligament 250 is then held in position by maintaining tension on the proximal portion of ligament 250 emerging from the bottom of tibia 125.

Figure 31:
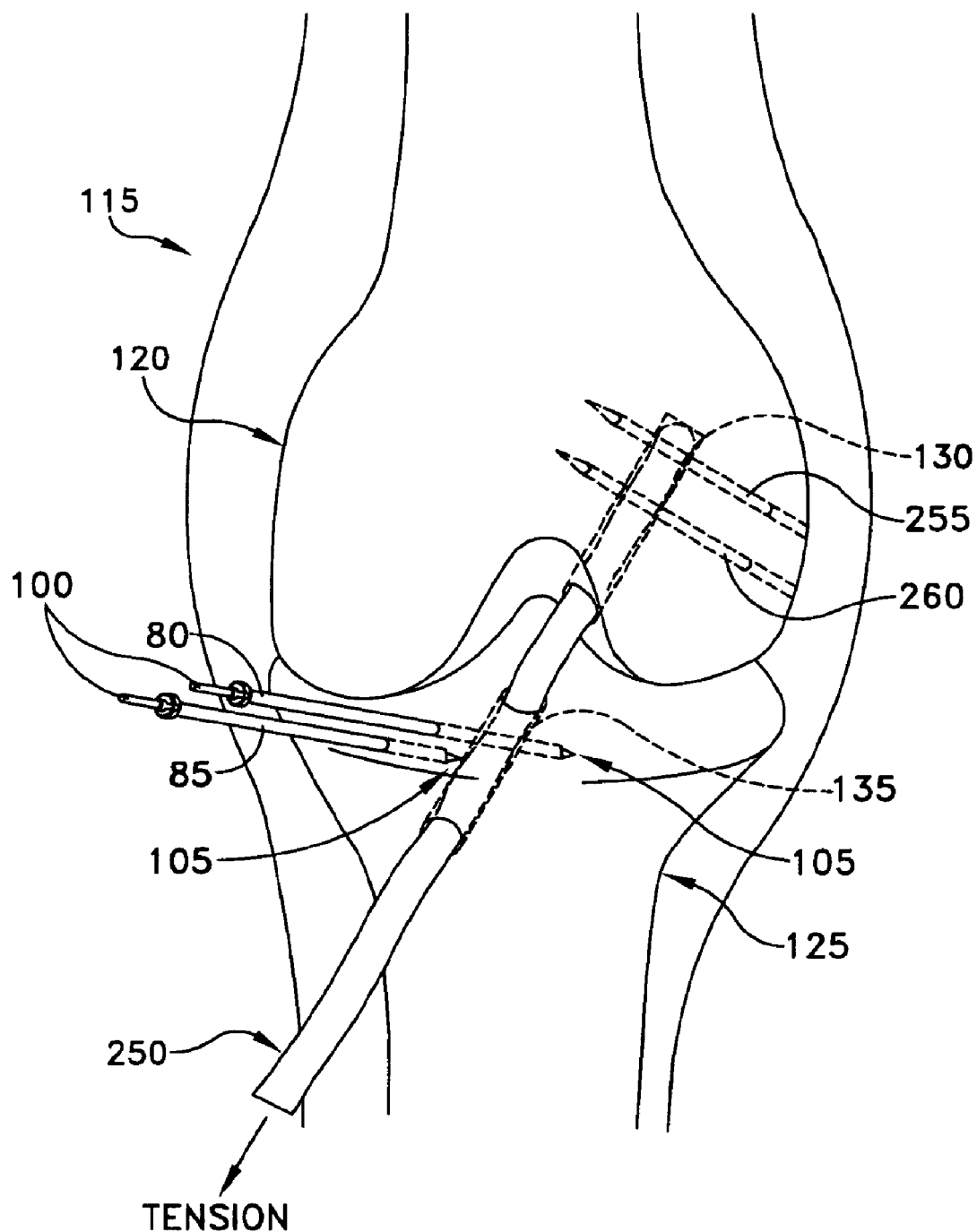
Figure 32:
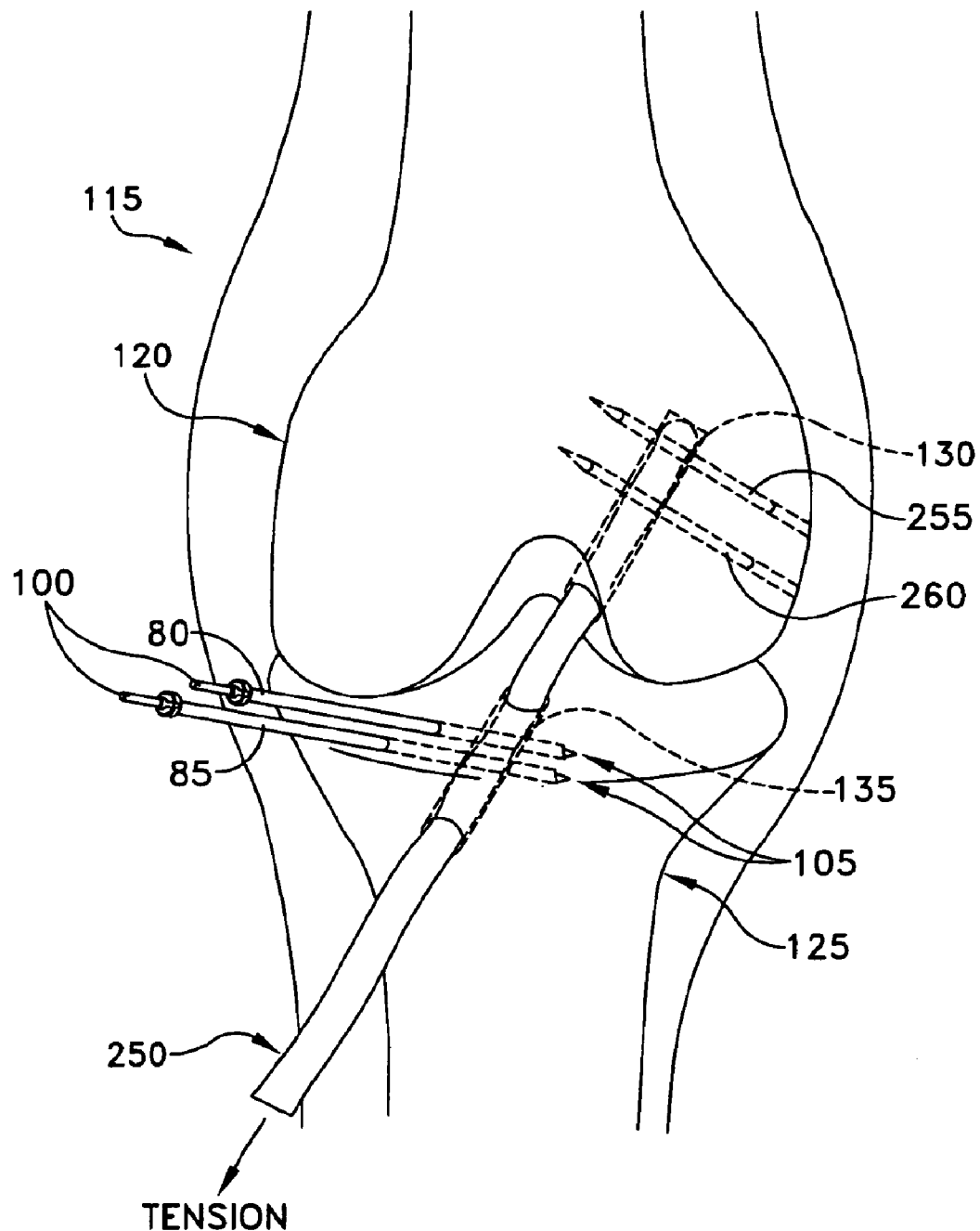
Figure 33:
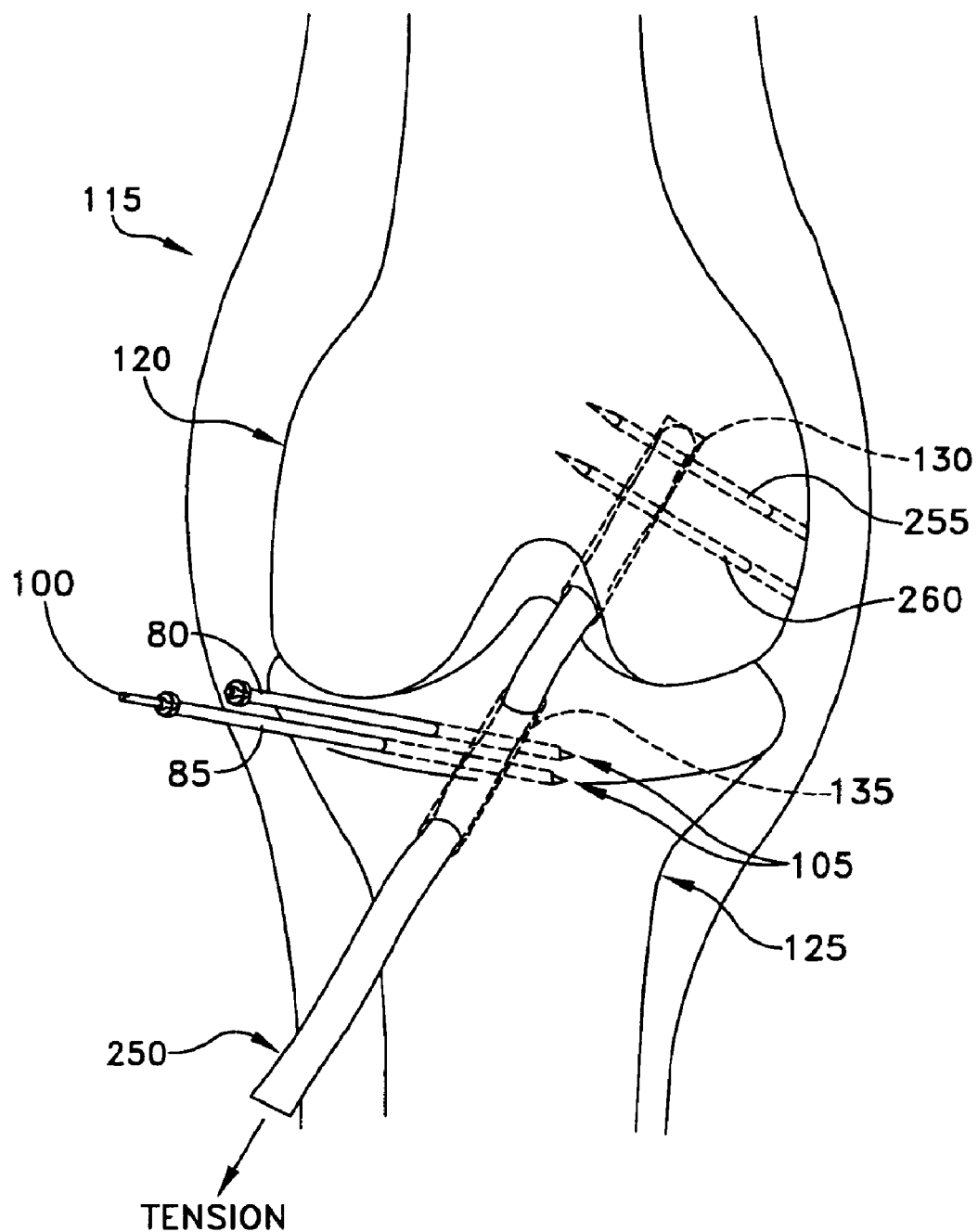

Next, graft ligament 250 is attached to tibia 125. More particularly, first trocar sleeve 80 and a trocar 100 are drilled through ligament 250, as shown in FIG. 31. Trocar 100 may then be removed from first sleeve 80, placed in second sleeve 85, and second sleeve 85 and trocar 100 drilled through ligament 250, as shown in FIG. 32. Alternatively, a second trocar 100 may be provided for use with second sleeve 85. In either case, after trocar sleeves 80 and 85 have been set, the trocar 100 (or trocars 100, if more than one trocar is used) may then be withdrawn from sleeves 80, 85 (FIG. 33). A first absorbable rod 255 is then inserted, by sliding rod 255 through trocar sleeve 80, into a position extending through ligament 250. Sleeve 80 may then be withdrawn from ligament 250 and tibia 125, leaving first absorbable rod 255 in place in tibia 125 and extending through ligament 250. Similarly, a second absorbable rod 260 is then slid into place through sleeve 85. Sleeve 85 is then removed, leaving second absorbable rod 260, along with first absorbable rod 255, extending through ligament 250 so as to lock ligament 250 into place in tibial tunnel 135, as shown in FIG. 34.

Now referring to FIGS. 35-38, there is shown a bone tunnel reference guide 265 for placement of at least one cross-pin (not shown in FIGS. 35-38) in a bone tunnel such as the tibial tunnel of a knee joint. Bone tunnel reference guide 265 may be used in procedures to fix graft ligaments (including both soft tissue grafts and bone block grafts) in bone tunnels. Bone tunnel reference guide 265 comprises an L-shaped member 270 having a base portion 275 and an arm portion 280. The arm portion 280 extends transversely to, and preferably is normal to, base portion 275.

Bone tunnel reference guide 265 further comprises a bone tunnel guide rod 285 having a first end 290 and a second end 295. Bone tunnel guide rod 285 includes a graduated index 300 between first end 290 and second end 295. Bone tunnel guide rod 285 includes a diametrically-extending, longitudinally-elongated passageway 305 intermediate its length and, at second end 295, is connected to base portion 275 of L-shaped member 270. In a preferred embodiment, bone tunnel guide rod 285 is cannulated at 306 (FIG. 35) for placement on a guidewire (not shown in FIG. 35). Bone tunnel guide rod 285 may be retained in a bore 315 formed in base portion 275 by a pin 320.

Still looking at FIGS. 35-38, a scale 325 is provided on arm portion 280 of L-shaped member 270. Scale 325 is coordinated with graduated index 300 on bone tunnel guide rod 285 as will hereinafter be discussed.

The present invent on may be practiced with cross-pins of any type, and is independent of the type of cross-pins used in a surgical procedure. Preferably, cross-pins of an absorbable nature are used in a given surgical procedure. Accordingly, the ACL reconstruction will hereinafter be discussed in the context of using absorbable pins, and in the context of using preferred apparatus for deploying such absorbable pins.

More particularly, in a preferred embodiment using absorbable cross-pins, a trocar sleeve guide member 330 is removably connectable to, and selectably adjustable along, scale 325 of arm portion 280 of L-shaped member 270. Trocar sleeve guide member 330 is provided with bores 335 extending therethrough. Bores 335 extend through a longitudinal axis 340 of bone tunnel guide rod 285. As such, at least one cross-pin is ultimately positioned in the tibia so as to pass through the tibial tunnel. More preferably, bores 335 are configured to intersect the longitudinal axis 340 of bone tunnel guide 285 just below the patient's tibial plateau. In this way, the at least one cross-pin will be deployed in the cortical portion of the tibia, adjacent to and just below the tibial plateau, and at the region of greatest bone strength. A set screw 345 may be used to releasably retain trocar sleeve guide member 330 in position along scale 325 of arm portion 280. Trocar sleeve guide member 330 is preferably formed in two halves releasably held together by a set screw 350, whereby trocar sleeve guide member 330 can be detached from first and second trocar sleeves 355, 360 passing through bores 335, as will hereinafter be discussed.

In another preferred embodiment, trocar sleeve guide member 330 is configured for direct placement of cross-pins, without the use of trocar sleeves 355, 360. In this case, cross-pins are inserted through, and guided by each of bores 335 in guide member 330.

Bone tunnel reference guide 265 is preferably used as follows. First, femoral tunnel 130 and tibial tunnel 135 (FIG. 14) are formed. Then the reference guide's guide rod 285 (FIGS. 35-38) is passed up tibial tunnel 135 and femoral tunnel 130 until the distal end 290 of guide rod 285 is in engagement with the distal end 165 of femoral tunnel 130 (FIG. 14). As this occurs, the reference guide's L-shaped member 270 will support trocar sleeve guide member 30 outboard of the patient's femur. Stabilization of the bone tunnel reference guide 265 is provided by applying a distally-directed force to guide rod 285, which is in engagement with the distal end 165 of femoral tunnel 130. This stabilization allows accurate placement of the cross-pins. Then an arthroscope is used to read the gradiated index 300 at the point at which guide rod 285 crosses the tibial plateau. Trocar sleeve guide member 330 is then set at a corresponding location along its own scale 325. In this respect it will be appreciated that gradiated index 300 is coordinated with scale 325 so that the axes of bores 335 (FIG. 35), and hence the cross-pins, will pass through the tibia at a desired position, such as through the tibia's cortical bone just below the tibial plateau.

Next, drill sleeves 355, 360 are used to set trocars 365, 370 into the tibia. Trocar sleeve guide member 330 is then separated into its two halves so as to free drill sleeves 355, 360 from reference guide 265, and the reference guide 265 is removed from the surgical site, e.g., by withdrawing it proximally off the guidewire. Then the graft ligament is pulled up into femoral tunnel 130 and tibial tunnel 135, the distal end of the graft ligament is made fast in femoral tunnel 130, and then drill sleeves 355, 360 are used to set absorbable cross-pins through the proximal end of the graft ligament, whereby to cross-pin the ligament to the tibia.

Figure 39:
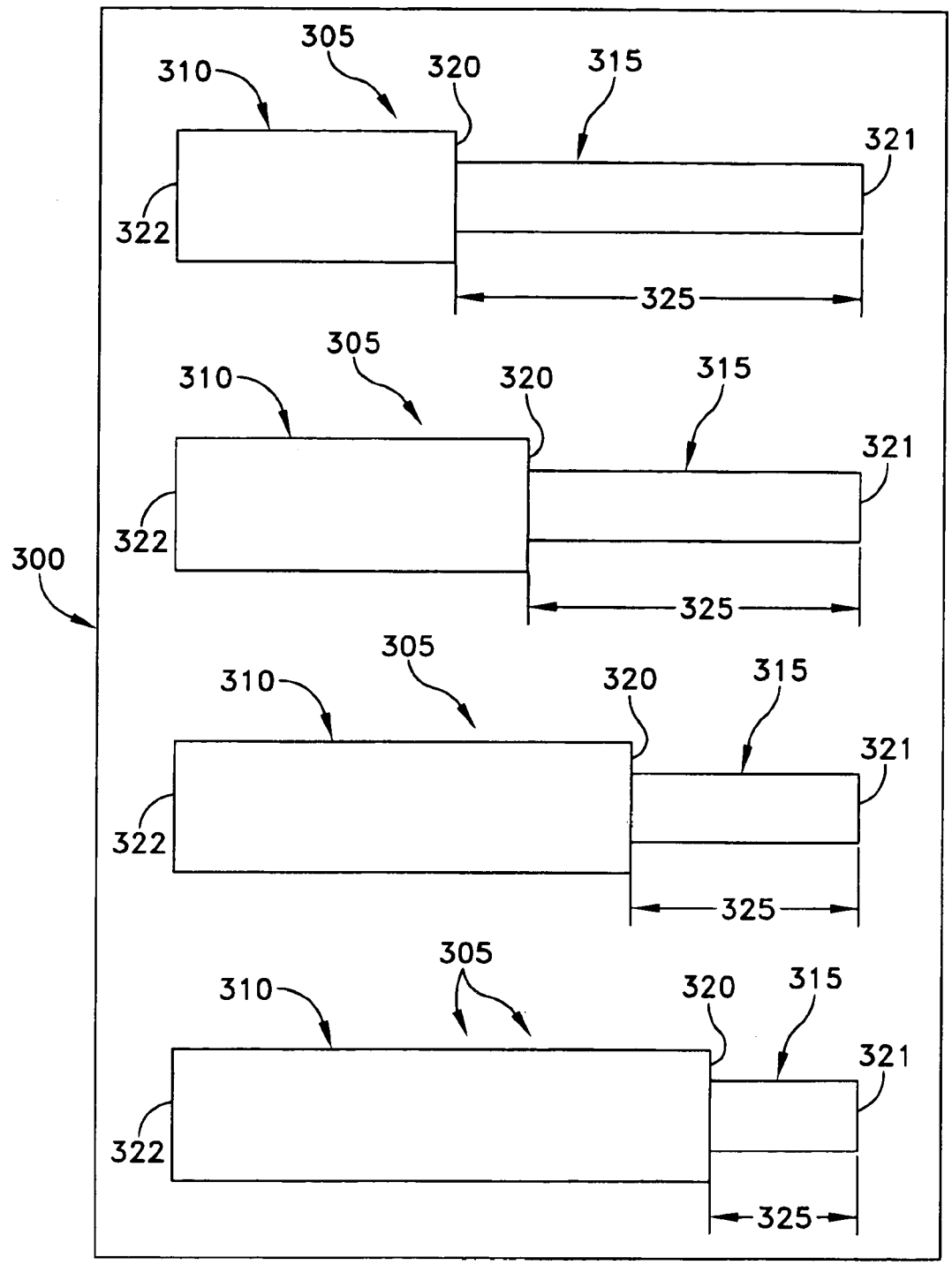
FIG. 39 is a schematic view of a kit of bone tunnel guide rods for use with a third embodiment of the present invention.
Figure 40:
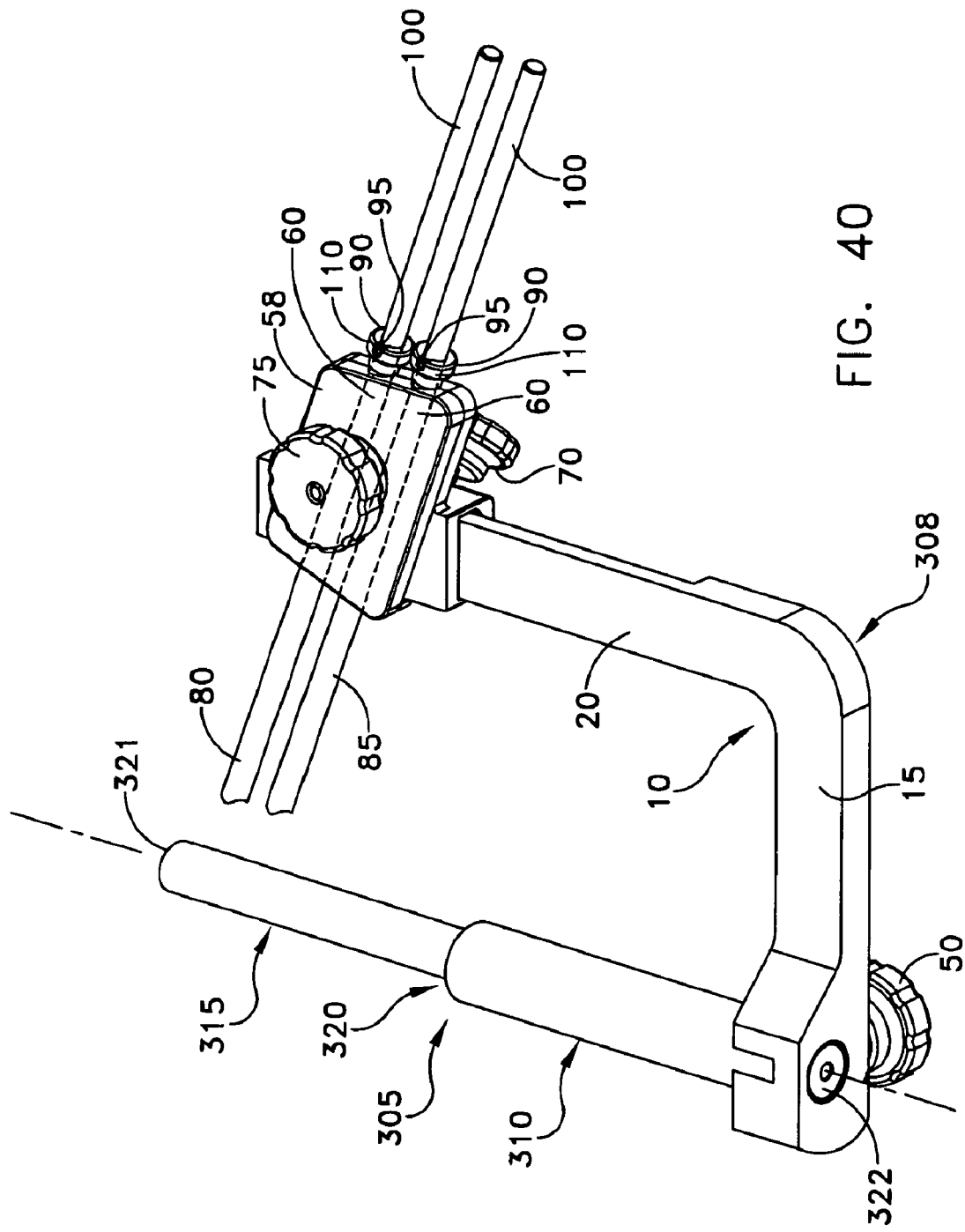
FIG. 40 is a schematic view showing one of the bone tunnel guide rods of FIG. 39 with an associated cross-pin guide assembly.

Now looking at FIG. 39, there is shown a kit 300 of bone tunnel guide rods 305 for use with a cross-pin guide assembly such as the cross-pin guide assembly 308 shown in FIG. 40. In one preferred form of the invention, cross-pin guide assembly 308 is similar to the cross-pin guide assembly 5 shown in FIGS. 1-10, except that bone tunnel guide rod 25 of cross-pin guide assembly 5 is replaced with one of the bone tunnel guide rods 305 shown in FIG. 39.

Each of the bone tunnel guide rods 305 includes a proximal end 310 and a distal end 315. As insertion limiting means 320, for limiting insertion into a bone tunnel, is located between proximal end 310 and distal end 315. Preferably insertion limiting means 320 comprises an annular shoulder formed intermediate the distal end 321 and the proximal end 322 of a given bone tunnel guide rod 305.

Insertion limiting means 320 are located at a given distance 325 from the distal end 321 of bone tunnel guide rods 305. Each kit 300 includes at least two bone tunnel guide rods, with the given distance 325 of each of the tunnel guide rods being different from one another. As such, selection is made from kit 300 by inserting at least one of the bone tunnel guide rods 305 into a bone tunnel and selecting the one of the bone tunnel guide rods 305 that has its distal end 321 aligned with the patient's tibial plateau when insertion limiting means 320 are in engagement with the front side of the patient's tibia. As a result of this construction, when that selected bone tunnel guide rod 305 is loaded in cross-pin guide assembly 308, bores 60 (FIG. 40), and hence the cross-pins, will be aimed at the thick cortical bone directly beneath the tibial plateau, whereby to enable secure and reliable tibial cross-pinning.

It is to be understood that the present invention is by no means limited to the specific applications thereof as herein disclosed and/or shown in the drawings. For example, for illustrative purposes, the inventive method and apparatus are described herein and illustrated with reference to the human knee joint. It is anticipated that the method and apparatus described herein will be particularly beneficial with respect to such operations. However, it will also be appreciated by those skilled in the art that the method and apparatus described herein will find utility with respect to mammals generally, and with respect to other bones as, for example, in shoulder joints or the like.

Furthermore, trocars 100 and 210 are disclosed herein as being in the form of a hard rod with a sharp tip for penetrating bone. Thus, for example, trocars 100 and 210 might comprise guidewires or K-wires with a pyramidal front point. Alternatively, however, the invention might also be practiced with trocars 100 and 210 comprising a twist drill, a spade drill and/or some other sort of drill.

Also it is contemplated that trocars 100 and/or 210 might be used with their associated guide member 58, rack assembly 145, reference guide 265, guide assembly 308 and/or apparatus 400 to set absorbable rods 255, 260, but without their associated sleeves 80, 85, and 200, 230, respectively. In this case, at least one trocar would always remain positioned in graft ligament 250 until at least one absorbable rod 255, 260 was positioned in the bone block.

If desired, it is also possible to practice the present invention using just one sleeve 80 and one trocar 100, or just one sleeve 85 and one trocar 100, or just one sleeve 200 and one trocar 210, or without using sleeves and/or trocars at all.

Numerous further variations, alterations, modifications and other derivations of the present invention will occur and/or become obvious to those skilled in the art in view of the foregoing detailed description of the preferred embodiments of the present invention. Accordingly, it is to be understood that the foregoing specification and the appended drawings are intended to be illustrative only, and not as limiting of the invention.

What is claimed is:

1. An apparatus for positioning at least one cross-pin in a bone through a bone tunnel, comprising:
   a guide member adapted to be inserted into a bone tunnel and having proximal and distal ends with an opening formed across the distal end;
   a movable element coupled to the guide member and selectively positioned along a length of the guide member so as to limit insertion of the guide member into a bone tunnel;
   a frame mated to the proximal end of the guide member at a location proximal to the movable element; and
   a drill guide located on the frame and including at least one hole formed therein and adapted to receive and support a drill sleeve such that the drill sleeve extends through the drill guide and through the opening formed across the distal end of the guide member.

2. The apparatus of claim 1, further comprising a drill sleeve disposed through the drill guide and the opening formed across the distal end of the guide member.

3. The apparatus of claim 2, wherein the drill sleeve comprises a trocar.

4. The apparatus of claim 2, further comprising at least one cross-pin disposable through the drill sleeve.

5. The apparatus of claim 4, wherein the at least one cross-pin is absorbable.

6. The apparatus of claim 1, further comprising a ratchet adapted to position the movable element on the guide member.

7. The apparatus of claim 1, wherein the opening in the distal end of the guide member is diametrical and longitudinally-elongated relative to the guide member.

8. The apparatus of claim 1, wherein the frame is substantially L-shaped with a base portion and an arm portion.

9. The apparatus of claim 8, wherein the guide member is releasably connectable to the base portion of the frame.

10. The apparatus of claim 8, wherein the base portion includes a bore and the guide member is retained in the bore formed in the base portion by a set screw.

11. The apparatus of claim 1, wherein the guide member is fixedly connected to the frame.

12. The apparatus of claim 1, wherein the guide member is cannulated along a longitudinal axis.

13. The apparatus of claim 8, wherein the drill guide is fixedly attached to the arm portion of the frame.

14. The apparatus of claim 8, wherein the drill guide is releasably attached to the arm portion of the frame.

15. The apparatus of claim 14, further comprising a set screw to releasably retain the drill guide on the arm portion of the frame member.

16. The apparatus of claim 14, further comprising a stop means for limiting movement of the drill guide along the arm portion of the frame member.

17. A method for fixing a ligament in a bone tunnel, comprising:
   forming a bone tunnel in a bone;
   inserting a guide member into the bone tunnel;
   positioning a movable element on the guide member against the bone at an open end of the bone tunnel to limit an insertion depth of the guide member into the bone tunnel;
   positioning at least one drilling mechanism through a drill guide supported on a frame coupled to the guide member, and through an opening formed in a distal end of the guide member to thereby drill at least one cross-pin hole transversely through the bone and across the bone tunnel; and
   inserting at least one cross-pin through the at least one cross-pin hole.

18. The method of claim 17, wherein the frame is attached to the guide member after positioning a movable element on the guide rod against the bone at the open end of the bone tunnel and before drilling at least one cross-pin hole transversely through the bone and across the bone tunnel.

19. The method of claim 17, wherein the frame member is attached to the guide member before inserting the guide member into the bone tunnel.

20. The method of claim 17, wherein the at least one drilling mechanism comprises at least one trocar extending through the drill guide on the frame and through the opening formed in the distal end of the guide member.

21. The method of claim 20, wherein the at least one cross-pin is inserted through a sleeve of the at least one trocar.

22. The method of claim 17, wherein inserting a guide member into the bone tunnel comprises advancing the guide member over a guide wire extending through the bone tunnel.

23. The method of claim 22, further comprising, prior to inserting at least one cross-pin, removing the guide member and leaving the guide wire extending through the bone tunnel, and pulling the guide wire out of the bone tunnel to pull a ligament graft attached to the guide wire into the bone tunnel.

24. The method of claim 23, wherein the at least one cross-pin is inserted through the ligament graft to anchor the ligament graft in the bone tunnel.

* * * * *

UNITED STATES PATENT AND TRADEMARK OFFICE
CERTIFICATE OF CORRECTION

PATENT NO. : 7,655,011 B2  Page 1 of 1
APPLICATION NO. : 11/088250
DATED : February 2, 2010
INVENTOR(S) : Whittaker et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 681 days.

Signed and Sealed this

Twenty-third Day of November, 2010

David J. Kappos
*Director of the United States Patent and Trademark Office*